(12) United States Patent
Rassoli

(10) Patent No.: US 7,104,797 B2
(45) Date of Patent: Sep. 12, 2006

(54) ROTATIONALLY IMMOBILIZED DENTAL IMPLANT AND ABUTMENT SYSTEM

(76) Inventor: Jeff Rassoli, 2737 E. Regal Park Ave., Anaheim, CA (US) 92806

( * ) Notice: Subject to any disclaimer, the term of this patent is extended or adjusted under 35 U.S.C. 154(b) by 301 days.

(21) Appl. No.: 10/390,864

(22) Filed: Mar. 18, 2003

(65) Prior Publication Data

US 2004/0185417 A1    Sep. 23, 2004

(51) Int. Cl.
  *A61C 8/00*        (2006.01)
(52) U.S. Cl. ...................................... 433/173; 433/174
(58) Field of Classification Search ................ 433/173, 433/174, 175; 403/359, 361; D24/156
  See application file for complete search history.

(56) References Cited

U.S. PATENT DOCUMENTS

| 4,571,111 | A | * | 2/1986 | Keogh | ......................... 403/282 |
| 5,195,892 | A | * | 3/1993 | Gersberg | .................... 433/174 |
| 5,334,024 | A | | 8/1994 | Niznick | |
| 5,433,606 | A | | 7/1995 | Niznick et al. | |
| 5,829,977 | A | | 11/1998 | Rogers et al. | |
| 5,984,680 | A | * | 11/1999 | Rogers | ........................ 433/173 |

OTHER PUBLICATIONS

Restorative Catalog 3I; (nlt Feb. 18, 2002); Worry-Free Restorations; Gold Standard ZR™ Abutment Design, Pg; vi.
Replace™ Product Catalog, May 2001; Nobel Biocare; Front Cover.
Patented Products of Core-Vent/Paragon; May 10, 2001, Paragon Newsletter; p. 2 of 7.
Paragon Implant Company Taper-Lock™ External Hex System Catalog; Feb. 1998; pp. 3 and 4.
Paragon Implant Company AdVent™ and Screw-Vent ® Implant Systems Catalog; Mar. 2000; pp. 3, 4, and 5.
Esthetics and Osseointegration; ISBN 0-9623064-0-1; 1989 pp. 40 and 41.

* cited by examiner

*Primary Examiner*—Gary O'Connor
*Assistant Examiner*—Candice C. Stokes
(74) *Attorney, Agent, or Firm*—Charles H. Thomas

(57) ABSTRACT

An endosseous dental implant system employs an implant member designed to be embedded into the jawbone of a patient at a location vacated by a missing tooth, and a mating abutment member. Both the abutment member and the implant member have mutually facing gingival ends. A socket of uniform, noncircular cross section throughout is defined into the gingival end of either the implant member or the abutment member while a post of corresponding cross-sectional configuration extends from the gingival end of the other member. At least one, and possibly a plurality, of transversely directed projections are formed on the post. These projections are small enough to allow the post to enter the socket in close fitting, seated engagement therewith, but large enough to create an interference fit between the post and the socket to obstruct twisting of the post within the socket. Apart from the transversely extending projections, the post has a uniform cross sectional shape and dimensions throughout its length.

8 Claims, 26 Drawing Sheets

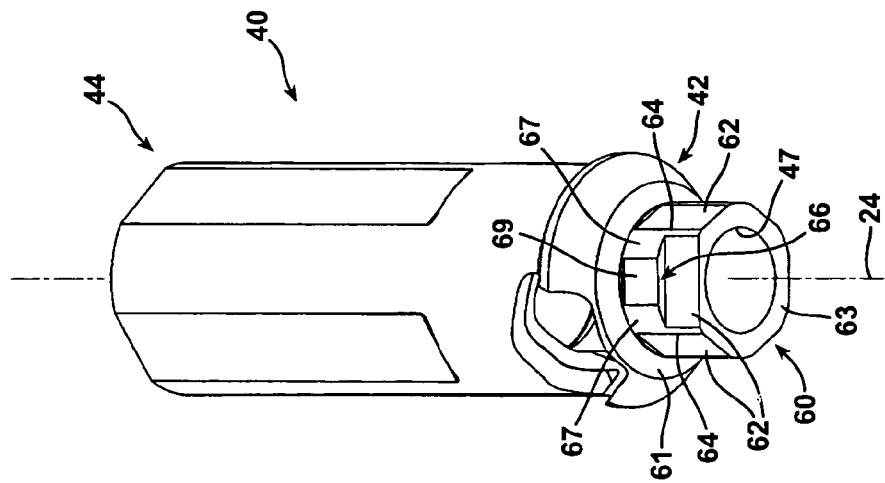
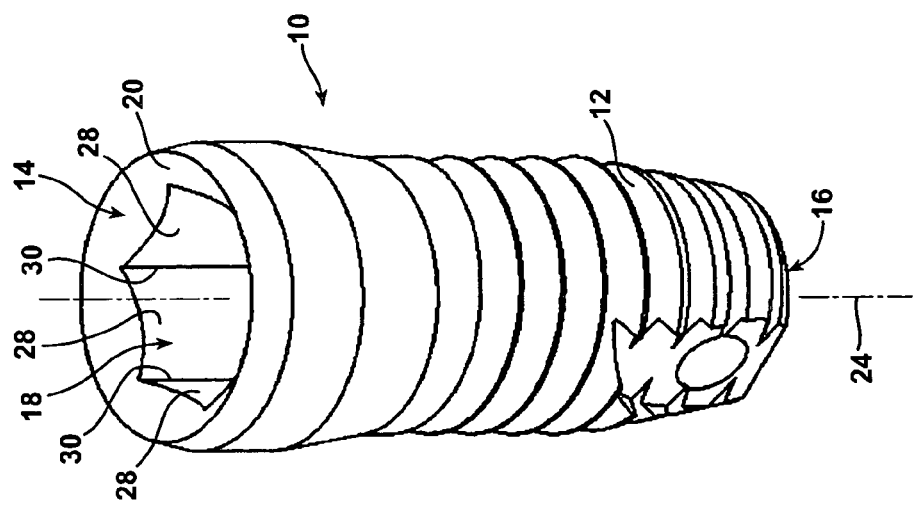

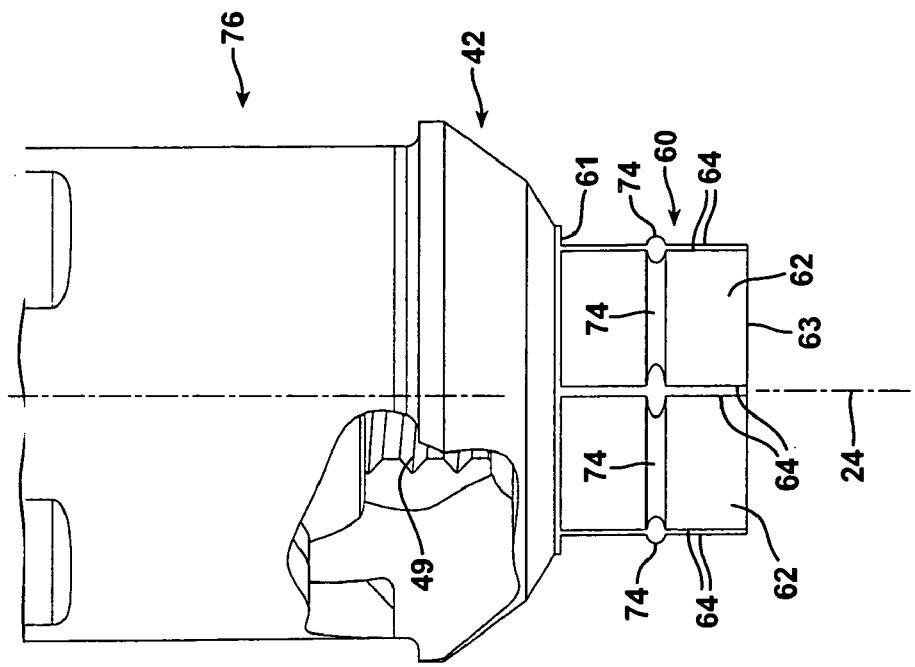
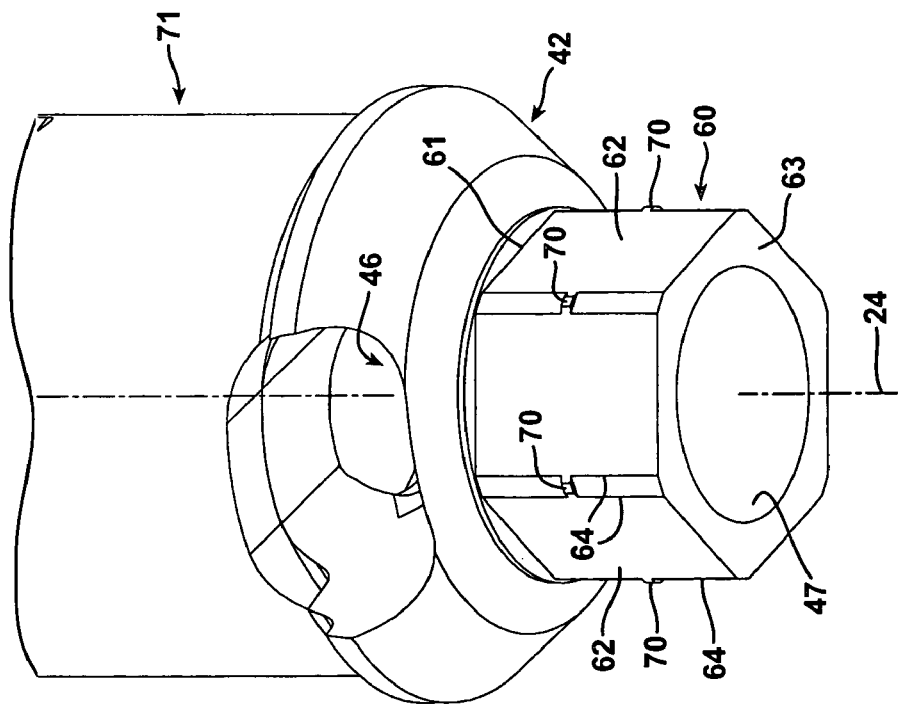

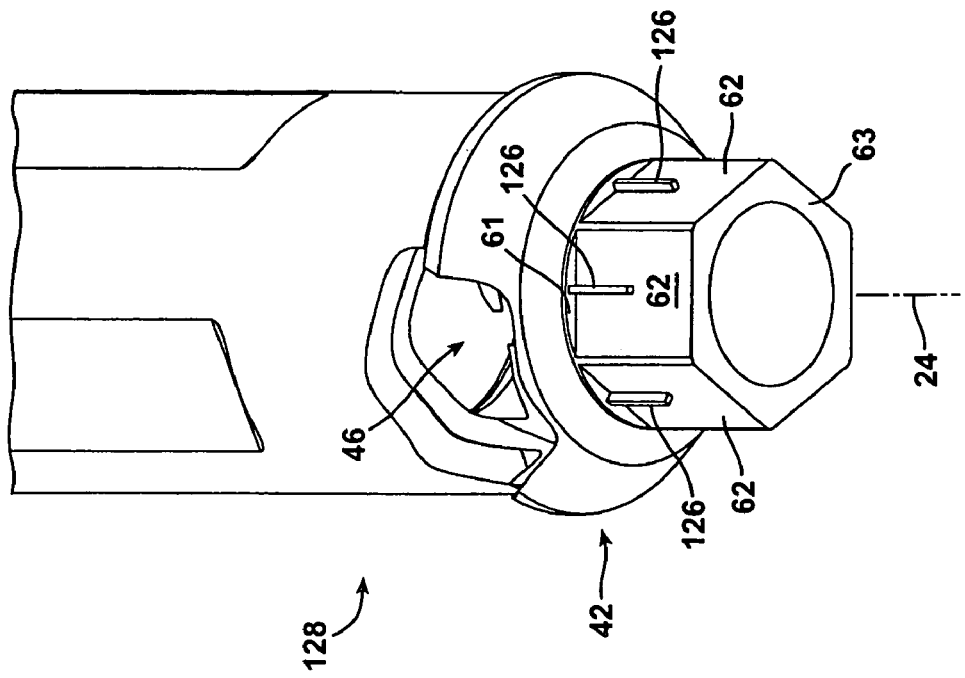
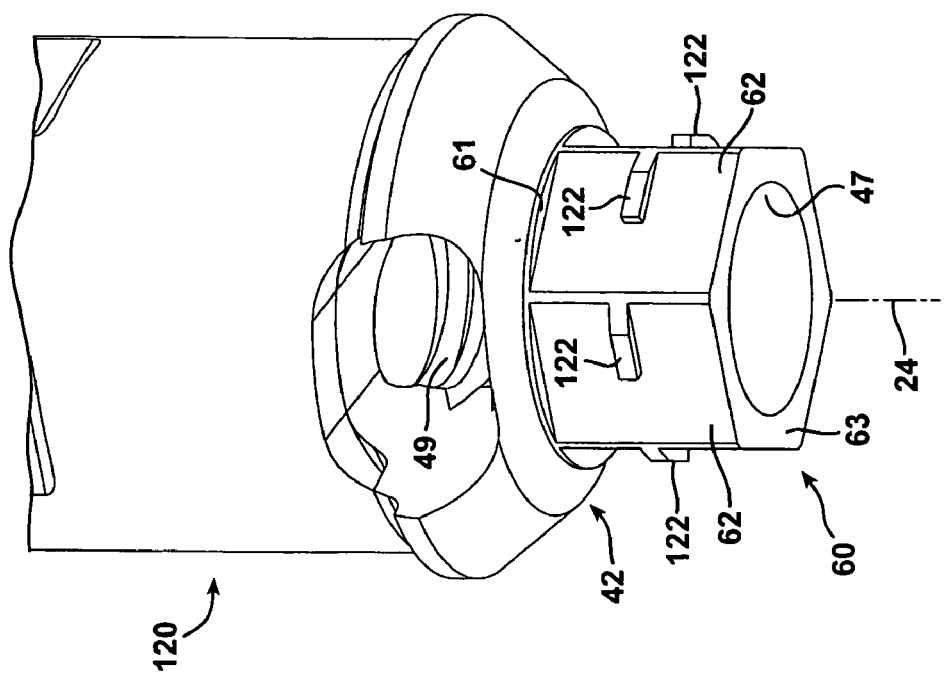

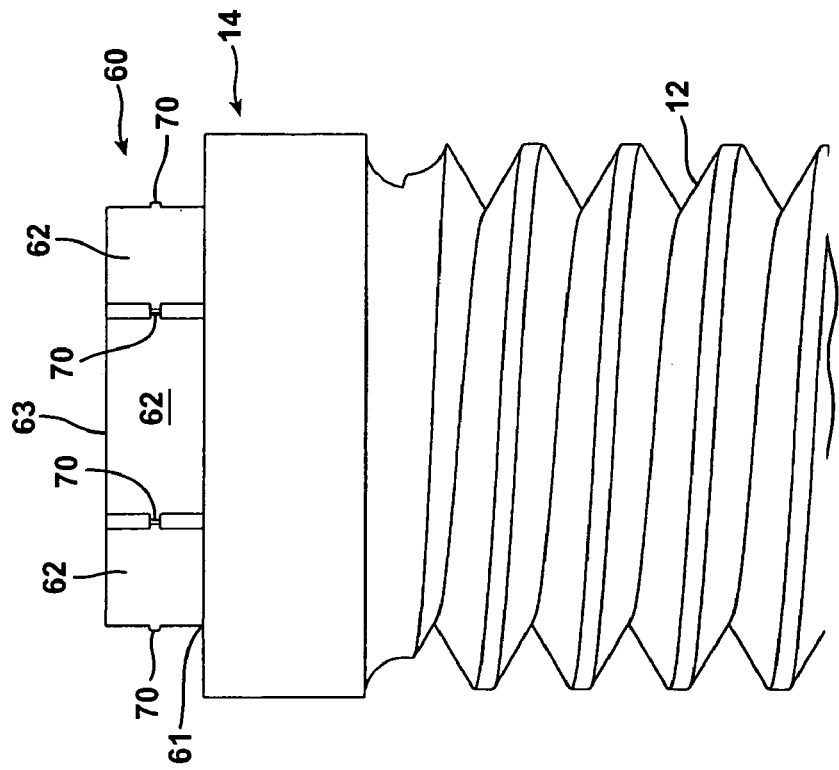
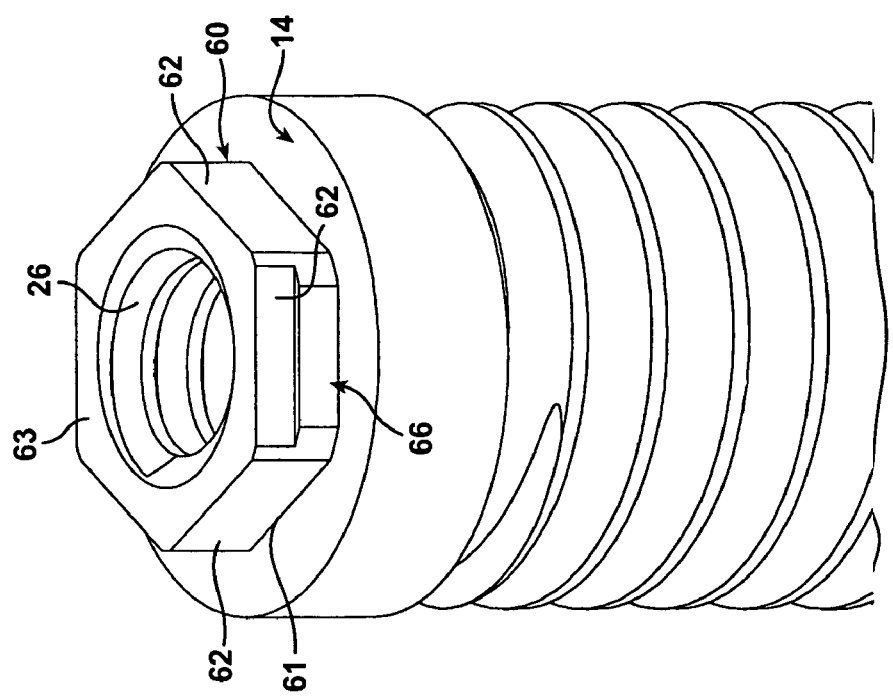

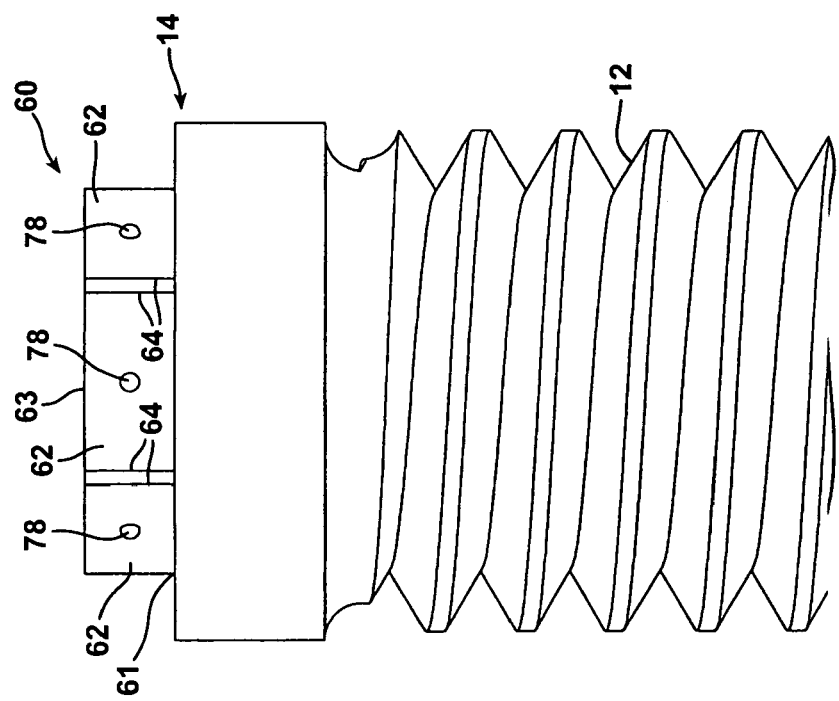
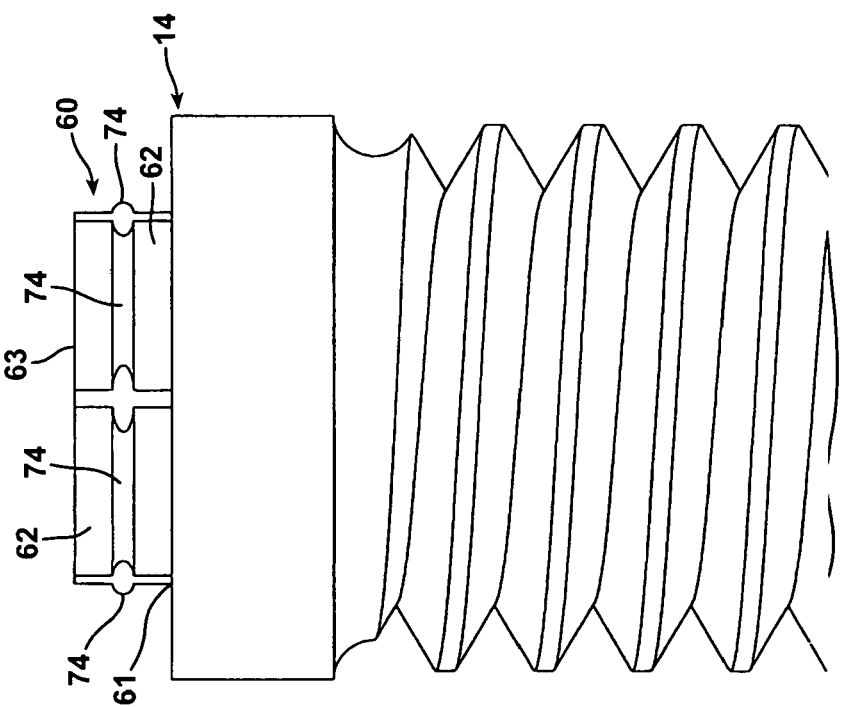

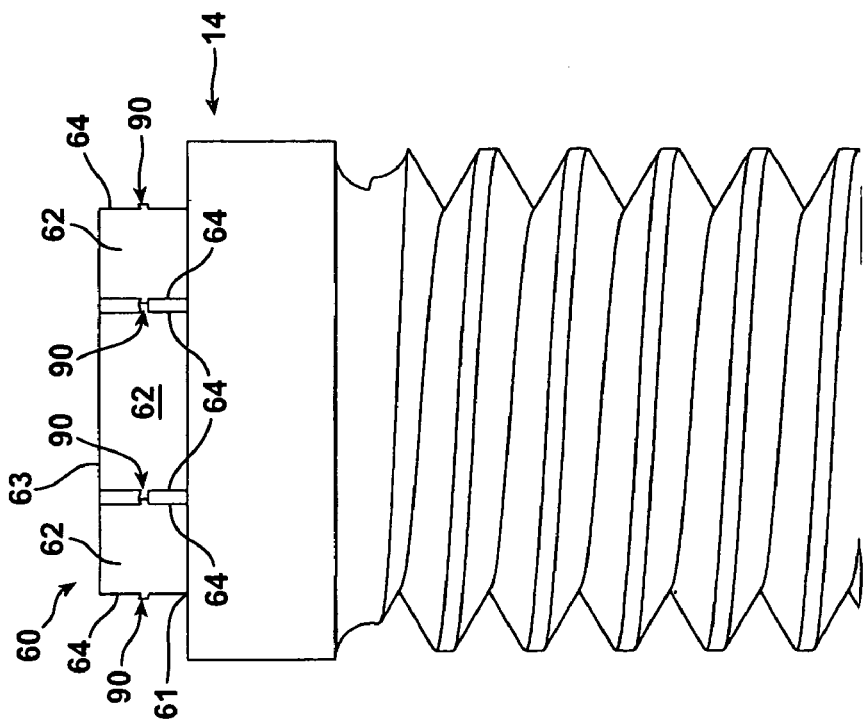
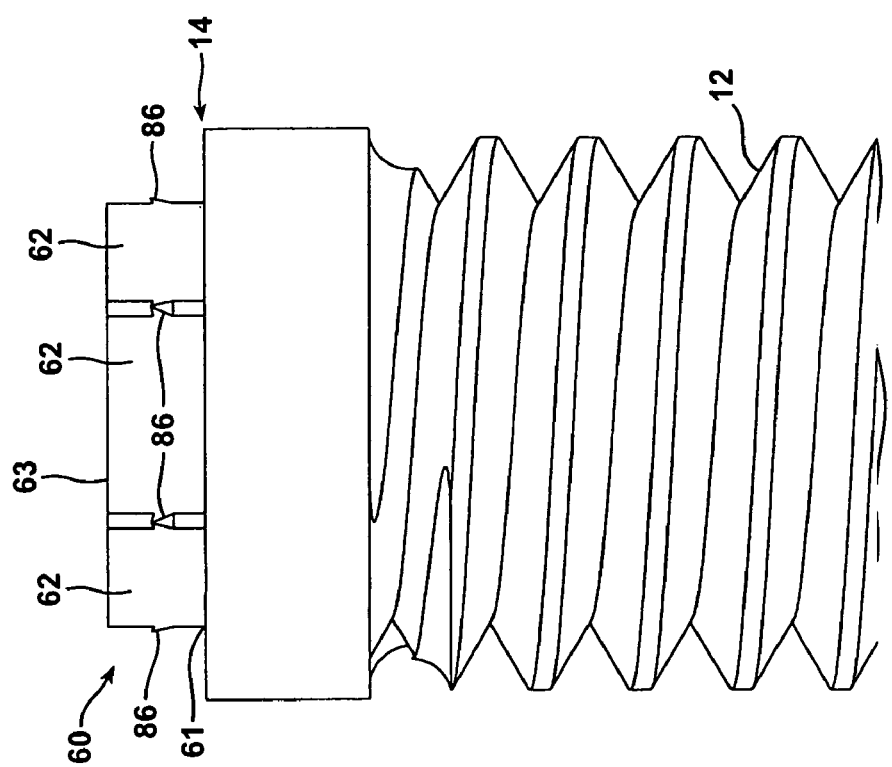

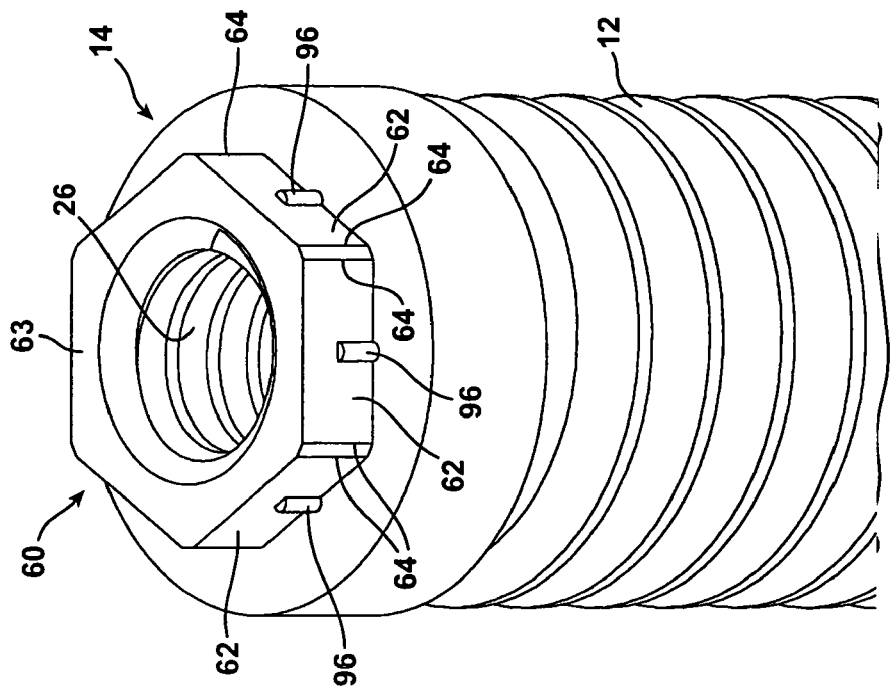
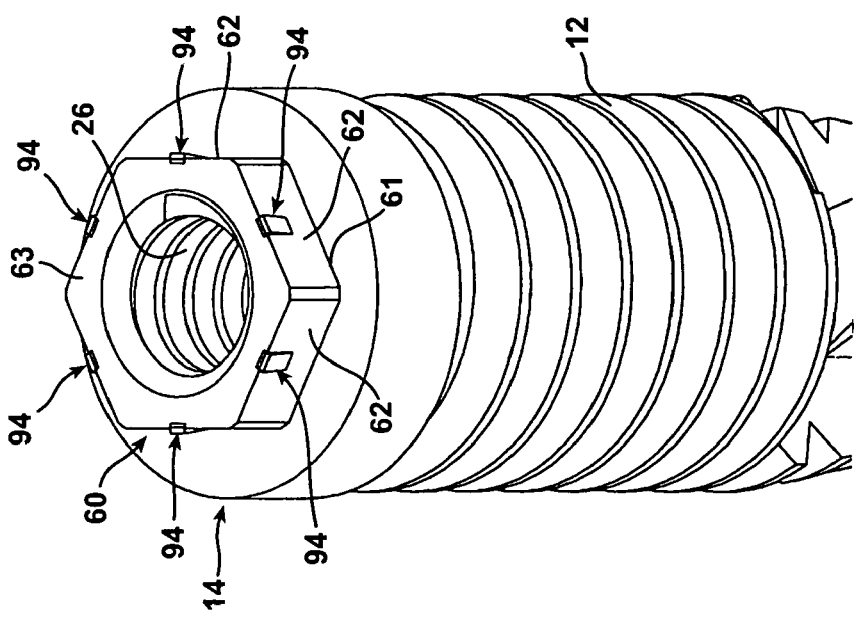

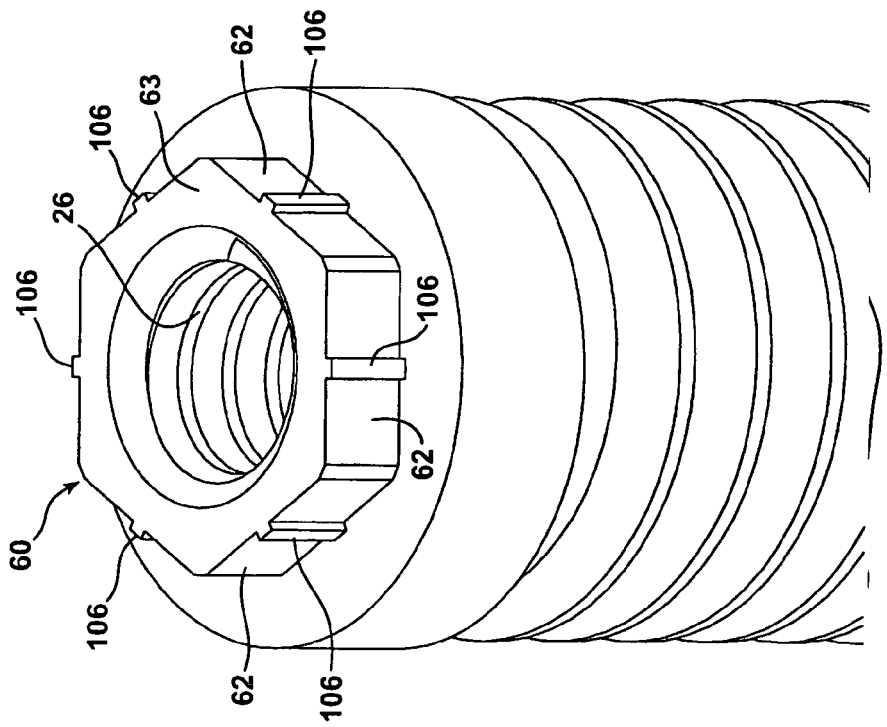

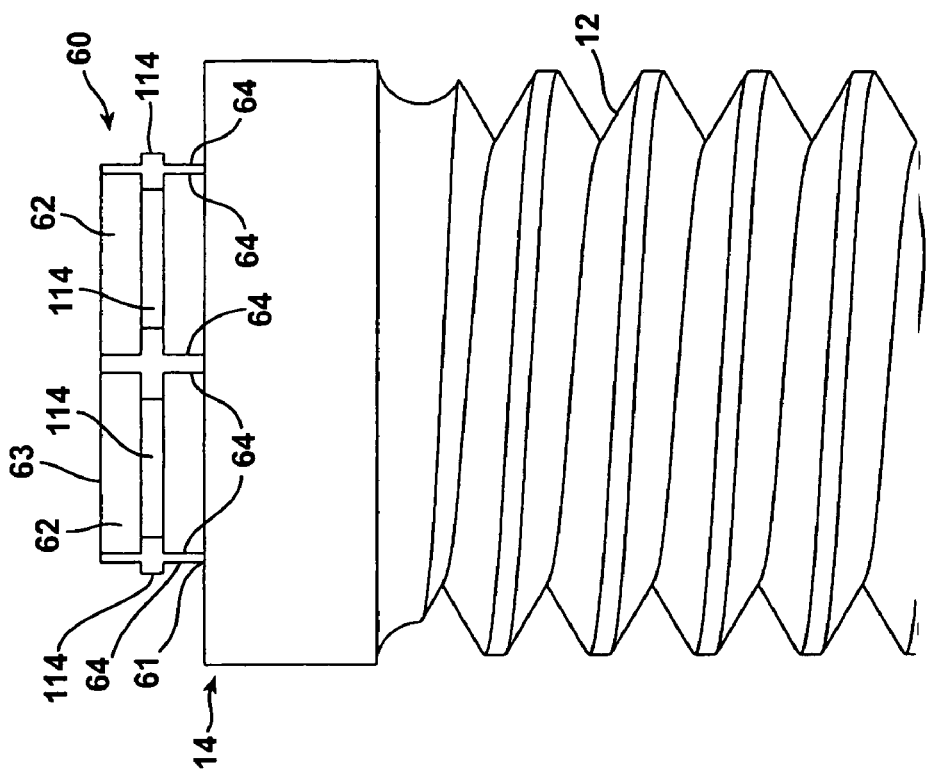
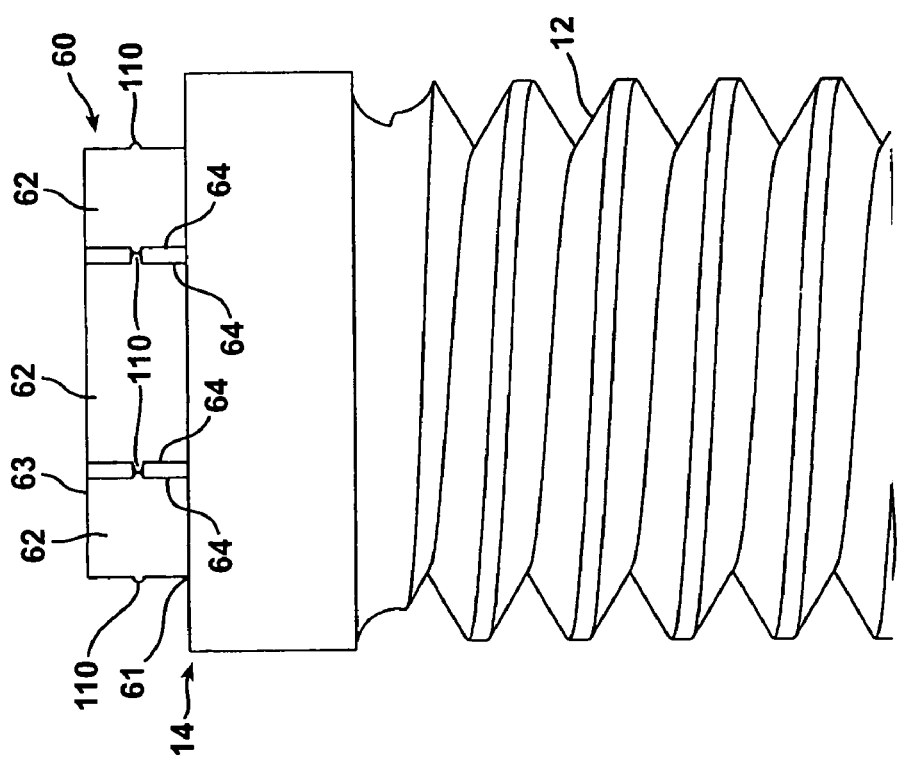

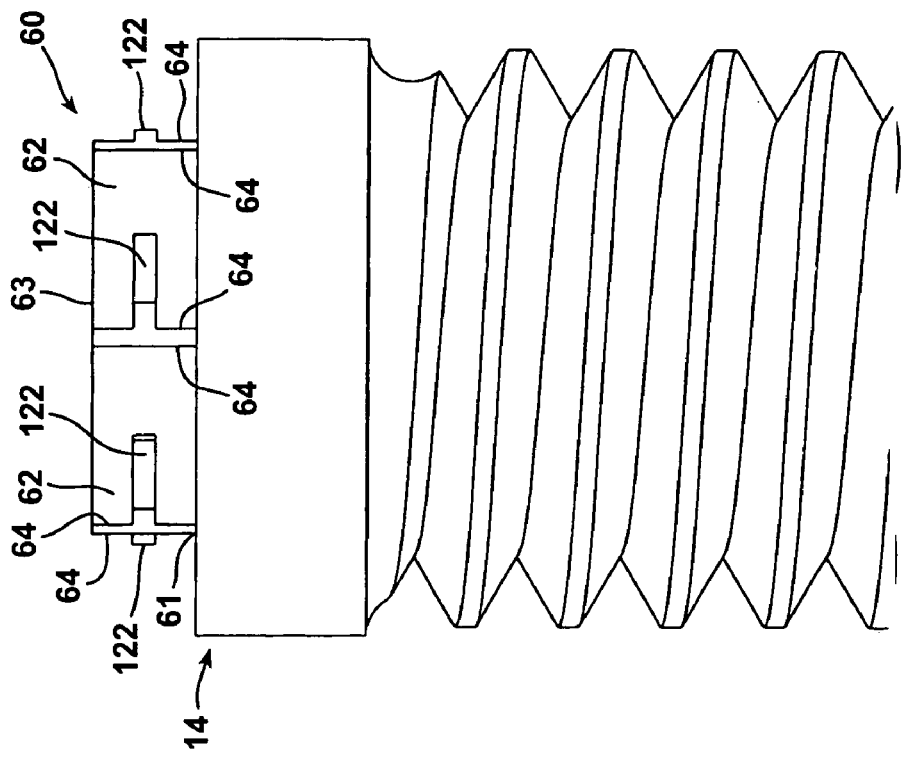
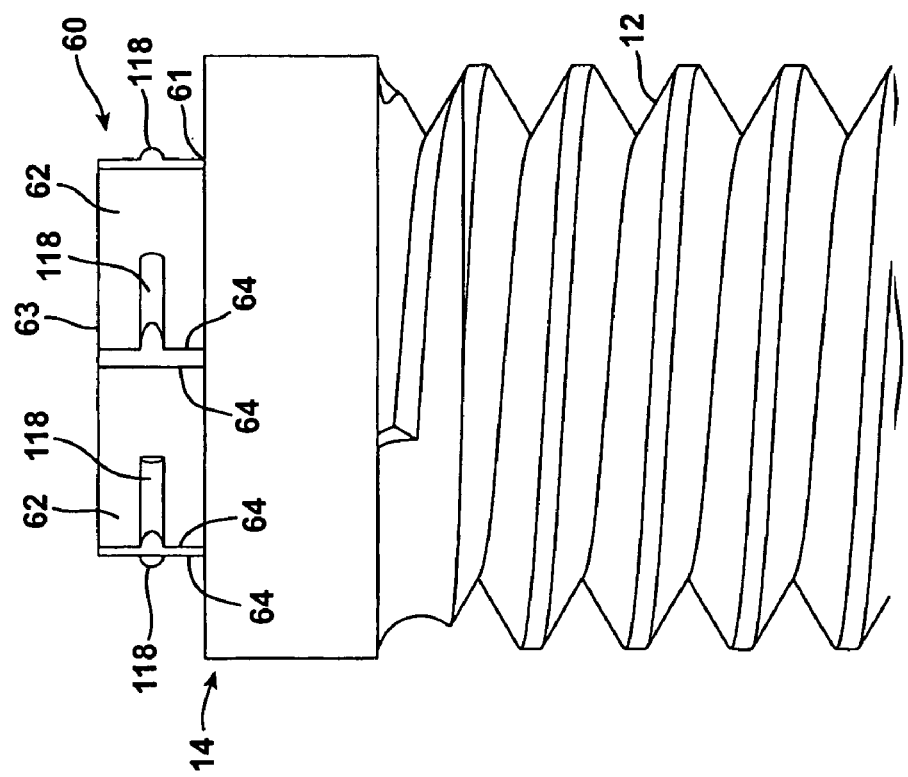

ROTATIONALLY IMMOBILIZED DENTAL IMPLANT AND ABUTMENT SYSTEM

BACKGROUND OF THE INVENTION

1. Field of the Invention

The present invention relates to osseodontic dental implant systems for tooth replacement in orthodontic patients.

2. Description of the Prior Art

In the field of orthodontics there are several techniques for tooth replacement. Crowns are widely employed for this purpose. However, dental crowns require a sturdy foundation. In the simplest, most desirable and least costly procedure the natural structure of the root of a tooth is utilized as the foundation to which the crown is anchored. However, in some instances, this is impractical since a tooth may be so badly damaged due to disease or injury that the entire tooth must be removed.

In such a situation one option is the use of an endosseous dental implant system. In such a system an implant member is inserted into the jaw of a patient. Very typically the implant member will be externally threaded with self-tapping screw threads that anchor the implant member into the bone of the jaw underlying the patient's gums. The implant member may be internally tapped to receive a screw.

The implant member has opposing gingival and osseous ends. That is, the implant member is of a generally cylindrical, externally threaded configuration with an internally tapped blind bore therein. The open end of the bore is at the gingival end of the implant member which resides at the patient's gum when the implant member is installed. The opposite, osseous end penetrates into the bone structure of the patient's jaw.

A conventional osseous dental implant system also includes an abutment member. The abutment member also has opposing ends which may be referred to as the gingival and coping support ends. The gingival end of the abutment member faces and mates with the gingival end of the implant member. The abutment member includes an internal, longitudinal bore with openings at both of its ends and with a bearing ledge defined within its structure. A coping, which is an artificial tooth or crown, is ultimately permanently attached to the coping support end of the abutment. A screw is utilized to attach the abutment member to the implant member. The externally threaded shank of the screw extends through the longitudinal bore through the structure of the abutment member and is threadably engaged with the internal threads of the blind, tapped bore in the implant member. The head of the screw rests upon the bearing ledge in the structure of the abutment member to firmly, and ultimately permanently, attach the abutment member to the implant member.

It is extremely important for the abutment member to be totally immobilized relative to the implant member. In early systems one difficulty that occurred was that the abutment member would twist relative to the implant member, thus creating angular misalignment of the artificial tooth about the axis of the fastening screw. To remedy this problem the implant member and the abutment member were fashioned with a socket of noncircular cross section in one of the members and a post of corresponding noncircular cross section in the other of the members. When the abutment member is placed in face-to-face contact with the implant member, the gingival ends of both members mate with each other. That is, the post enters the socket in snug fitting relationship therewith.

The post and socket are both of corresponding noncircular cross section, typically polygonal in shape. For example, both the post and socket may have a hexagonal cross section. Because the post and socket are both of noncircular shape, it was thought that the abutment member could be completely immobilized from any rotational movement relative to the implant member.

However, certain difficulties with this prior system occurred. Specifically, due to the necessary dimensional tolerance that must exist for a post to be inserted into a socket, conventional implant and abutment systems of the type described still experience some slight twisting of the abutment member relative to the implant member. To eliminate this, another system was devised. Specifically, the mating polygonal post and socket arrangement was modified so that the post was tapered downwardly in a convergent manner in a direction toward the abutment. That is, the cross section of the post was configured to have a progressively reduced cross-sectional area proceeding from its base toward its distal extremity that was inserted into the abutment member. While this arrangement did address the problem of rotation of the post relative to the socket, it creates another problem in that it is possible for an interstitial gap to exist between the faces of the gingival ends of the implant and socket members surrounding the socket opening and the post. On the other hand, it is also possible with such a construction for the post to fail to reach the bottom of the socket, thereby creating a cavity into which fluids in the patient's mouth can seep.

SUMMARY OF THE INVENTION

The present invention involves a unique construction of dental implant and abutment members in an endosseous dental implant system that avoids the problems described with conventional dental implant systems. Specifically, the unique construction of the dental implant and abutment members according to the present invention provides a system that prevents rotation of the abutment member relative to the implant member, and which also ensures that the post of one of the mating abutment and implant members seats completely in the socket of the other member. As a consequence, the present invention provides an improved osseodontic arrangement for seating a dental abutment member relative to a dental implant member.

In one broad aspect the present invention may be considered to be an improved combination of an endosseous dental implant member and a mating abutment member, both having mutually facing gingival ends. The gingival end of one of these members has a socket of noncylindrical shape and uniform cross section throughout defined therein and facing the gingival end of the other of these members. The other of the two mating members has, at its gingival end, a post of corresponding, mating noncylindrical shape.

According to the improvement of the invention the post is equipped with at least one transversely directed protrusion therefrom and is otherwise of uniform cross section throughout. The post fits snugly into the socket with the transverse projection pressing outwardly against the interior wall of the socket to create an interference fit between the socket and the post. The term "transversely", as utilized herein may be defined as a direction perpendicular to the longitudinal axis of alignment of the internally tapped bore through the abutment member or perpendicular to the longitudinal axis of alignment of the blind bore in the implant member, both of which reside in mutually coaxial alignment.

Preferably, the post is formed on the gingival end of the abutment member and the socket is formed in the gingival end of the implant member. However, the reverse construction is also possible. That is, the post may be formed on the gingival end of the implant member and the socket may be formed in the gingival end of the abutment member.

The post and socket may be constructed in a variety of geometrical cross-sectional shapes, as long as those shapes are noncylindrical. That is, both the post and the socket could be constructed with a semicircular cross section or with a key and keyway. Preferably, however, both the socket and the post have mating polygonal shapes forming planar wall surfaces with straight, linear edges therebetween on the post and straight, linear corners in the socket.

While the post in the combination of the invention may be fabricated with a single lateral or transversely directed projection, there may be a plurality of projections. These may be located on planar wall surfaces of the post. The projections may be located either along the edges of the post between the planar wall surfaces that fit into the socket corners, or they may be located on the planar wall surfaces of the post between the edges of the post.

The transversely directed projections from the post are quite small relative to the size of the post and the socket and can have many different configurations. For example, the projections may be directed perpendicularly out from the post and may be formed as rounded nubs on the wall surfaces of the post. Alternatively, the projections may be formed as barbs on the post, inclined outwardly in divergent fashion toward the socket. The projections may have planar outer faces that diverge outwardly from planar wall surfaces of the post and toward the socket.

On the other hand, the transverse projections may be formed as teeth that increase in longitudinal cross section with radial distance from the axis of alignment of the post and socket. The teeth may be located at the longitudinal extremity of the post that fits into the deepest part of the socket. Alternatively, the transverse projections may be formed as longitudinally extending, semicylindrical ribs of rectangular cross section on the planar wall surface of the post. The ribs may extend the entire length of the post, or only part way along the length of the post. They may be located either at the distal tip that extends into the depth of the socket, at an intermediate location, or at the proximal or base end of the post, remote from the bottom of the socket.

The, projections may also be formed on the planar faces of the post as laterally extending ribs. These ribs may be of rounded or have a rectangular cross-sectional configuration and may extend all the way to the edges of the post at the demarcations between the planar faces thereof, or only part way across the planar faces. The term "laterally" as utilized herein may be defined as a direction lying in a plane that is perpendicular to the longitudinal axis of alignment of the tapped bores in the implant and abutment members.

In a preferred aspect the invention may be considered to be, in combination, an endosseous dental implant member and a mating abutment member, both having mutually facing gingival ends. The gingival end of one of the members has a socket of polygonal shape and uniform cross section throughout defined therein and facing the gingival end of the other of the members. The other of the implant and abutment members has at its gingival end a post of corresponding size and polygonal shape so as to seat snugly in the socket. The post has at least one transversely projecting protrusion that obstructs twisting of the post within the socket. The post is otherwise of uniform cross section throughout.

In still another aspect the invention may be considered to be an improvement in a dental implant system. Such a system employs an endosseous dental implant member having a gingival end and a mating abutment member having a gingival end facing the gingival end of the implant member. A socket of uniform, noncircular cross section throughout is defined into one of the members in the gingival end thereof. A post extends from the gingival end of the other member. The post has a noncircular cross section matching that of the socket so as to allow the post to fit snugly into the socket along a common axis of alignment. According to the improvement of the invention, at least one transversely directed projection is defined on the post. The transverse projection is short enough to allow the post to be completely seated in the socket. However, the transverse projection extends radially relative to the axis of alignment a sufficient distance to create an interference fit between the post and the socket.

By forming the post with one or more very short transversely extending projections, a dental implant system is created in which the post and socket are both of a basic, uniform cross section along their length, but the post is provided with at least one very slight transverse protrusion that obstructs any rotation of the abutment member once the post and socket of the abutment and implant members are engaged with each other with the post seated in the socket. That is, the protrusion extends out far enough from the surface of the post to create an interference fit between the post and the socket.

The invention may be described with greater clarity and particularity by reference to the accompanying drawings.

DESCRIPTION OF THE DRAWINGS

FIG. 1 is a perspective view of one embodiment of an implant constructed for use in the combination implant and abutment system of the invention.

FIG. 2 is a perspective view, partly broken away, illustrating a preferred embodiment of an abutment member designed for use in combination with the implant member illustrated in FIG. 1.

FIG. 3A is a perspective detail of the gingival end of the abutment member shown in FIG. 3.

FIG. 4 is an elevational detail, partially broken away, illustrating the gingival end of another alternative embodiment of an abutment member configured to fit into the socket of FIG. 1.

FIG. 15 is a perspective detail, partially broken away, illustrating the gingival end of another alternative embodiment of an abutment member configured to fit into the socket of FIG. 1.

FIG. 16 is a perspective detail, partially broken away, illustrating the gingival end of another alternative embodiment of an abutment member configured to fit into the socket of FIG. 1.

FIGS. 21 through 40 illustrate alternative embodiments of the invention in which the locations of the sockets and posts have been reversed on the implant members and abutment members and correspond, respectively, to the embodiments and assemblies illustrated in FIGS. 1 through 20.

DESCRIPTION OF THE EMBODIMENTS

Figure 3:
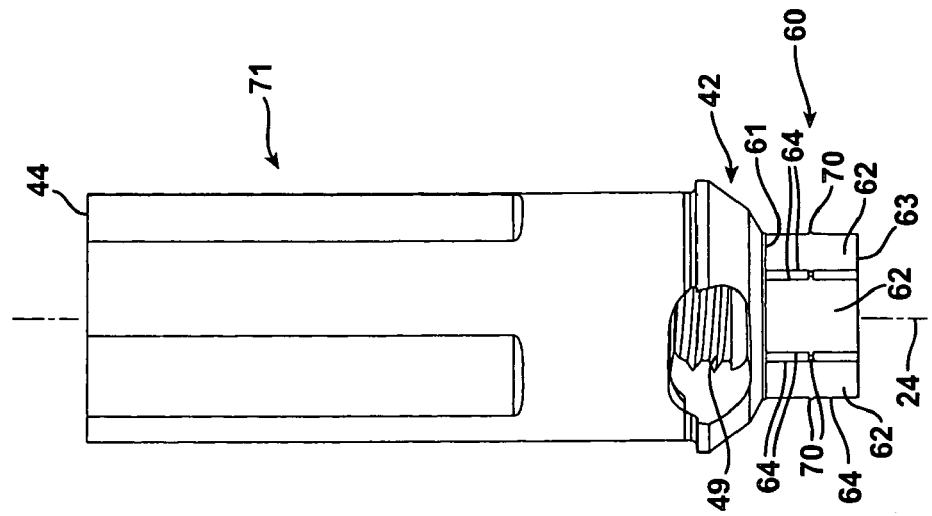
FIG. 3 is an elevational detail, partially broken away, illustrating one alternative embodiment of the gingival end of an abutment member configured for use with the implant illustrated in FIG. 1.

FIGS. 1 and 17 through 20 illustrate an endosseous dental implant member 10 of the type utilized for endosseous dental implants in the jaw of a patient. The endosseous dental implant member 10 is typically fabricated as a titanium structure having external threads 12 designed to be screwed into the jaw bone of a patient and penetrate into the bone to anchor the implant member 10 relative to the patient's jaw. The implant member 10 has a gingival end 14 and an opposite osseous end 16. When the implant member 10 is installed in the jaw of the patient, the osseous end 16 resides well into the jaw bone structure of the patient, while the gingival end 14 is located at the surface of the patient's gum in the recessed cavity therein vacated by the tooth being replaced.

A socket 18 is formed into the structure of the implant member 10 at the gingival end 14 thereof. The socket 18 has a uniform, noncircular cross section throughout, and is preferably of a polygonal configuration. In the embodiment illustrated in FIG. 1, the socket 18 is formed as a blind cavity or well having a uniform, hexagonal cross section throughout its length. The upper end of the socket 18 is open and terminates at a concave upwardly facing surface 20 surrounding the opening of the socket 18 at the gingival end 14 of the implant member 10. The terms "up", "upward", and "upwardly", as used herein, refer to a direction out and away from the patient's bone and toward the patient's mouth cavity, while the terms "down", "downward", and "downwardly", as used herein, refer to a direction into and toward the patient's bone and away from the patient's mouth cavity.

The floor 22 of the socket 18 is flat and perpendicular to the axis of alignment 24 of the socket 18. An internally tapped blind bore 26 is defined at the center of the floor 22 of the socket 18 and extends longitudinally along the axis of alignment 24 part way down, but not completely through the structure of the implant member 10.

The socket 18 has a hexagonal cross section so that each of its walls 28 is formed as a flat planar surface parallel to the axis of alignment 24. The socket walls 28 form longitudinal linear corners 30 that are also parallel to the axis of alignment 24.

Figure 2A:
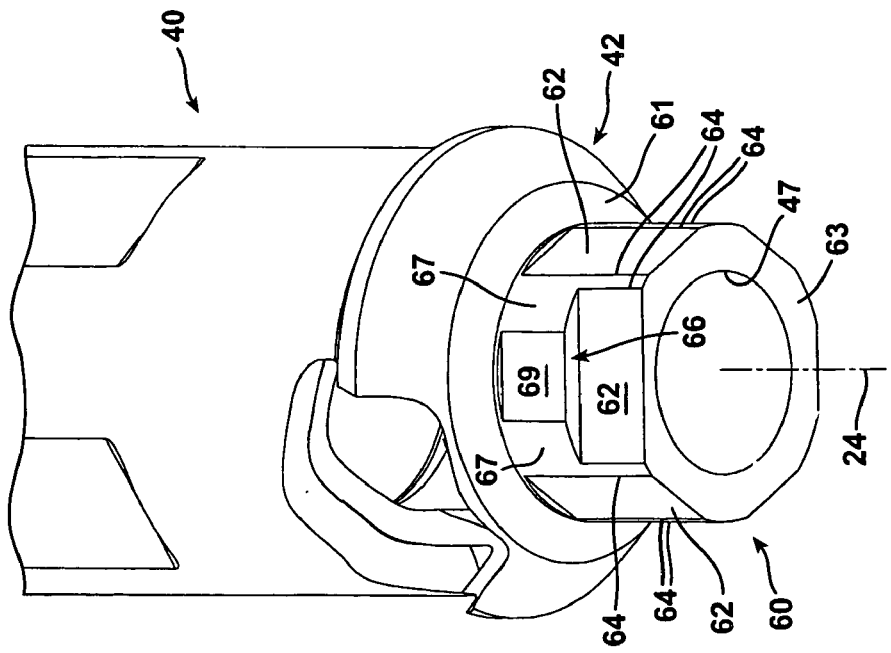
FIG. 2A is an enlarged perspective detail showing the lower portion of the abutment of FIG. 2.

The dental implant system of the invention also includes an abutment member such as the abutment member 40, shown in isolation in FIGS. 2 and 2A, that mates with the implant member 10, as illustrated in drawing FIGS. 17 through 20. The abutment member 40 has a generally cylindrical outer surface configuration with a gingival end 42 that resides in proximity to and is directed toward the jaw bone of the patient in the tooth cavity and an opposing upper, coping end 44 about which an artificial tooth is secured.

The abutment member 40 is formed with a central, axial, longitudinal bore 46 that extends throughout the length of the abutment member 40 from the gingival end 42 to the coping end 44. The upper portion 45 of the bore 46 has a smooth walled, cylindrical shape. The lower portion 47 of the bore 46 is of a reduced diameter and is internally tapped at 49 along a portion of its length to receive the threaded shank 48 of a clamping screw 50.

Figure 20:
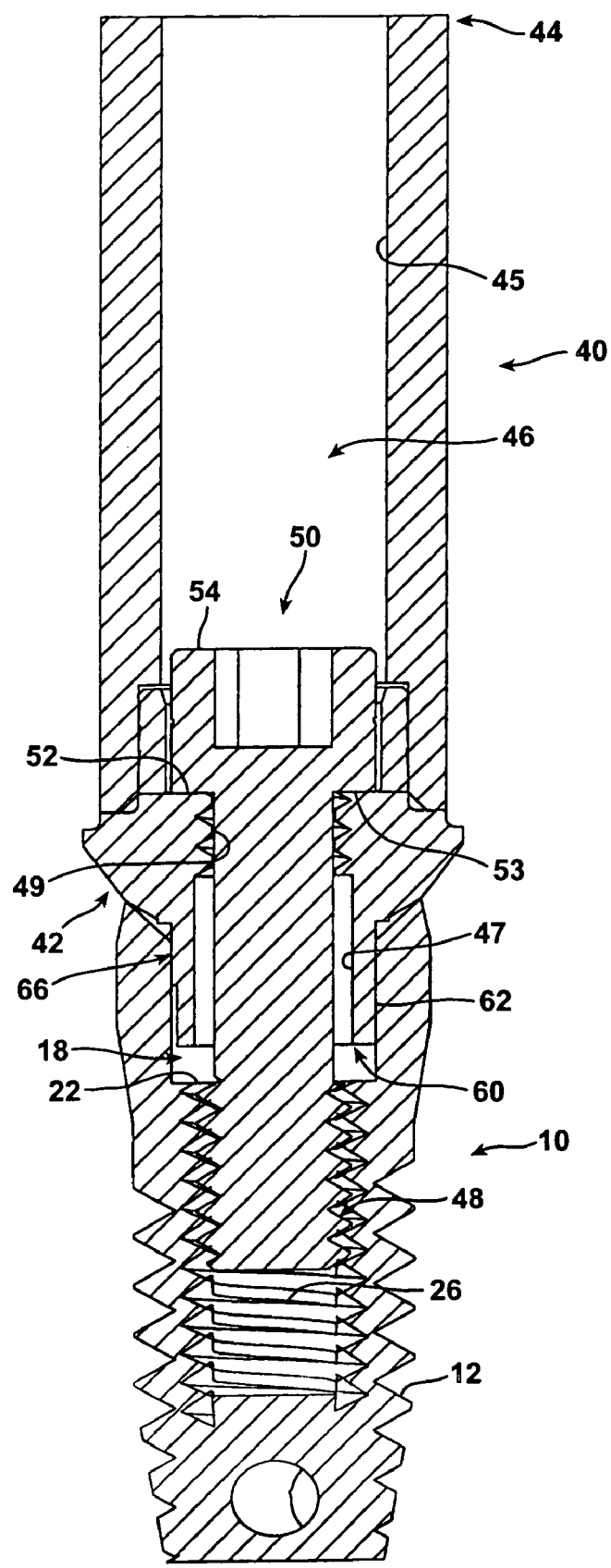
FIG. 20 is a sectional elevational view illustrating the implant of FIG. 1 and the abutment of FIG. 2 attached to each other as in an osseodontic dental implant.
Figure 22:
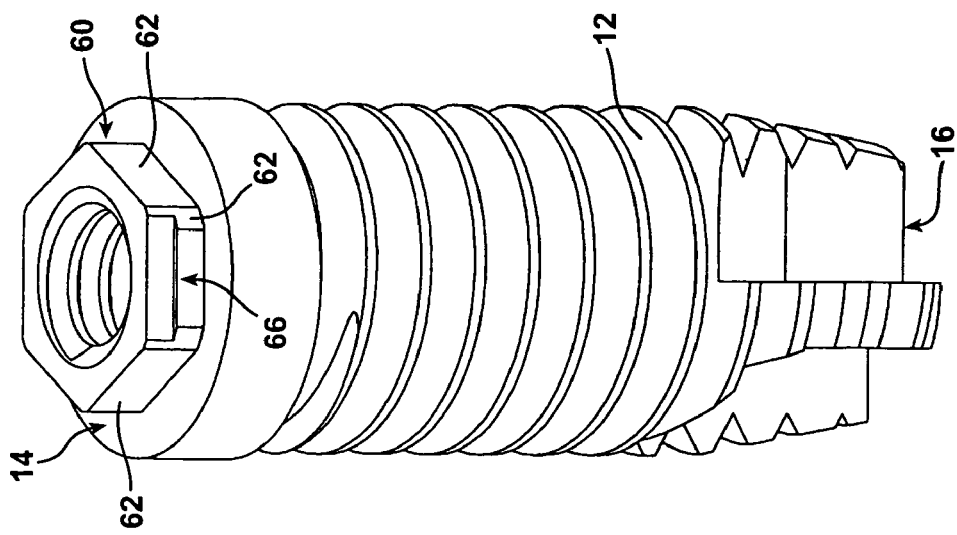
Figure 21:
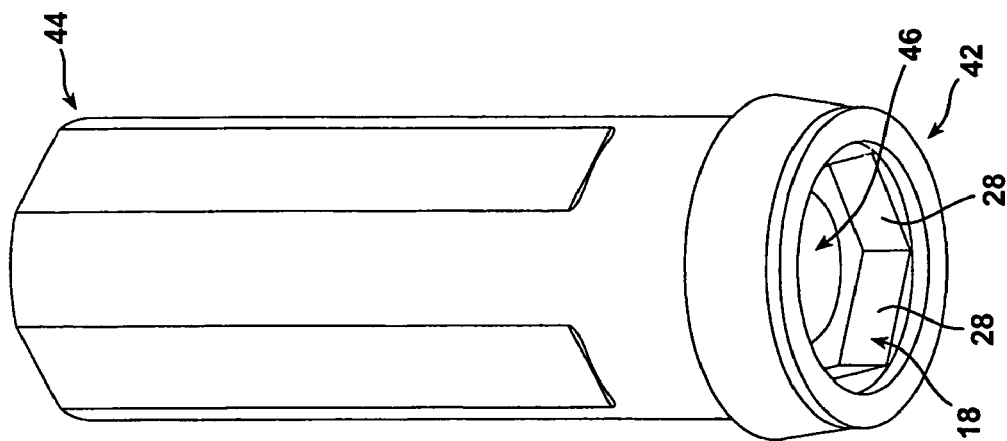
Figure 36:
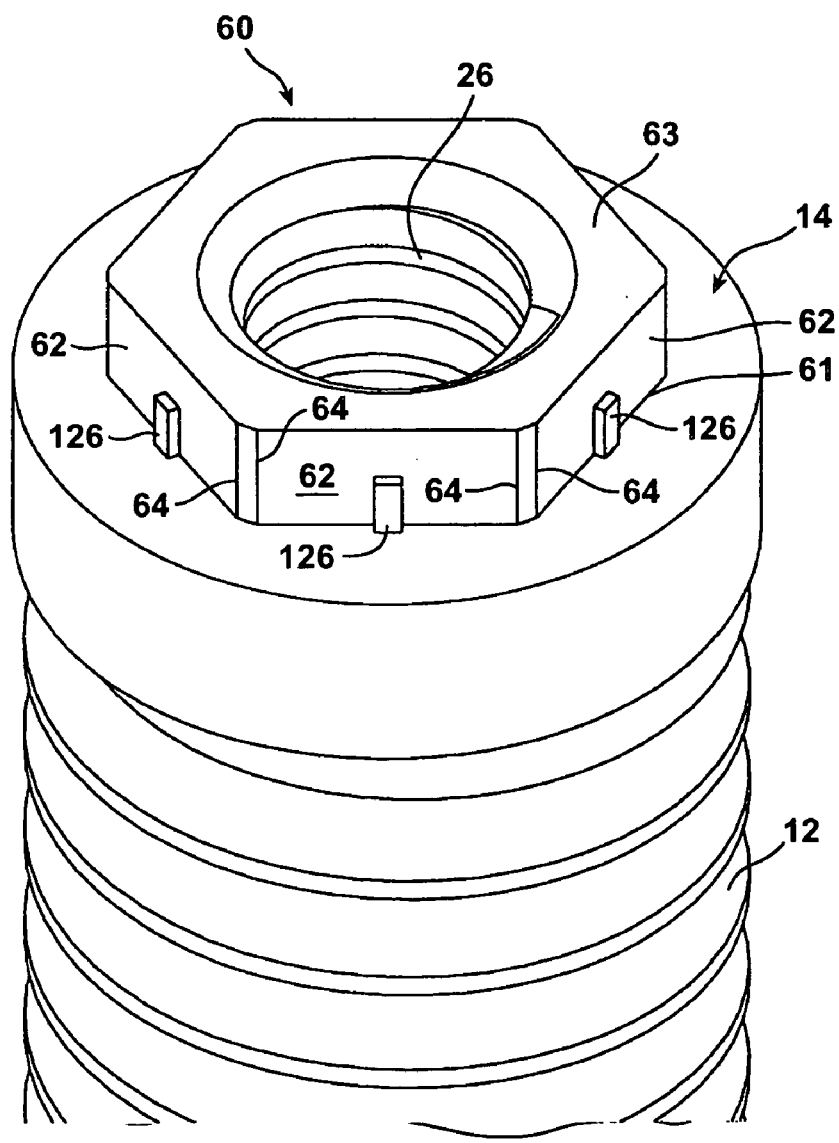
Figure 37:
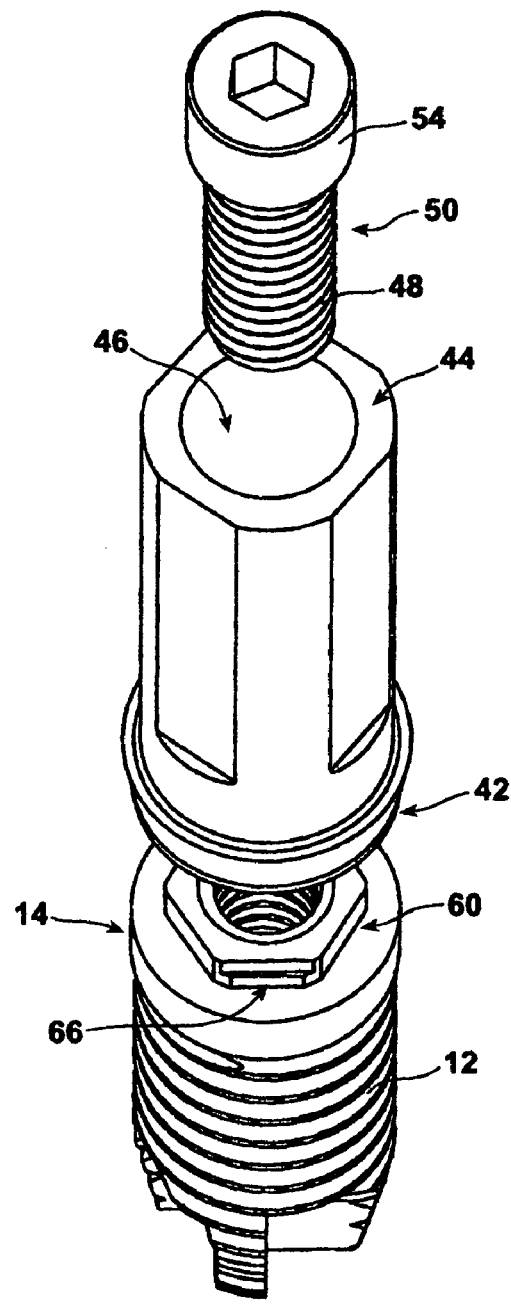
Figure 38:
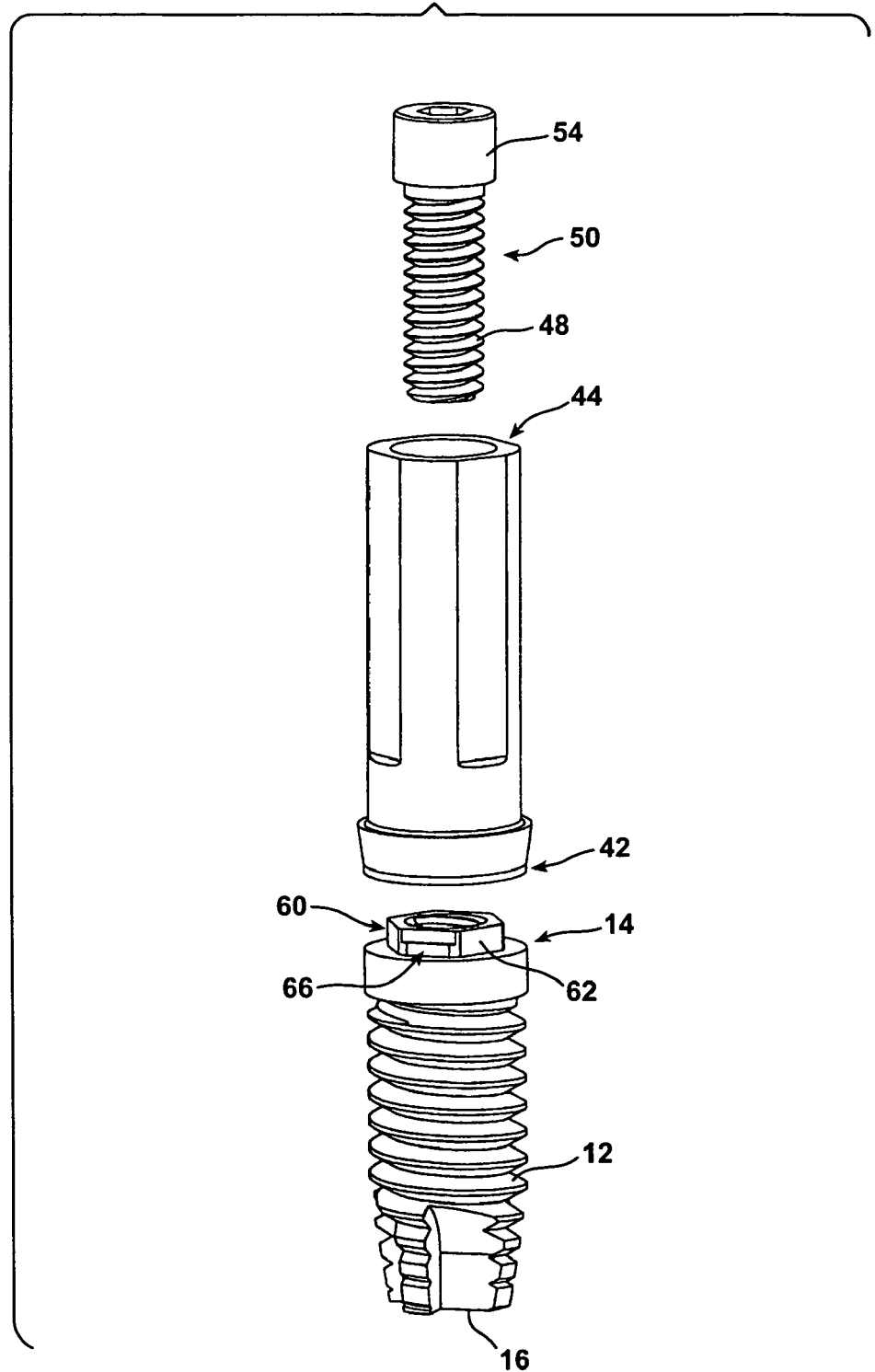
Figure 39:
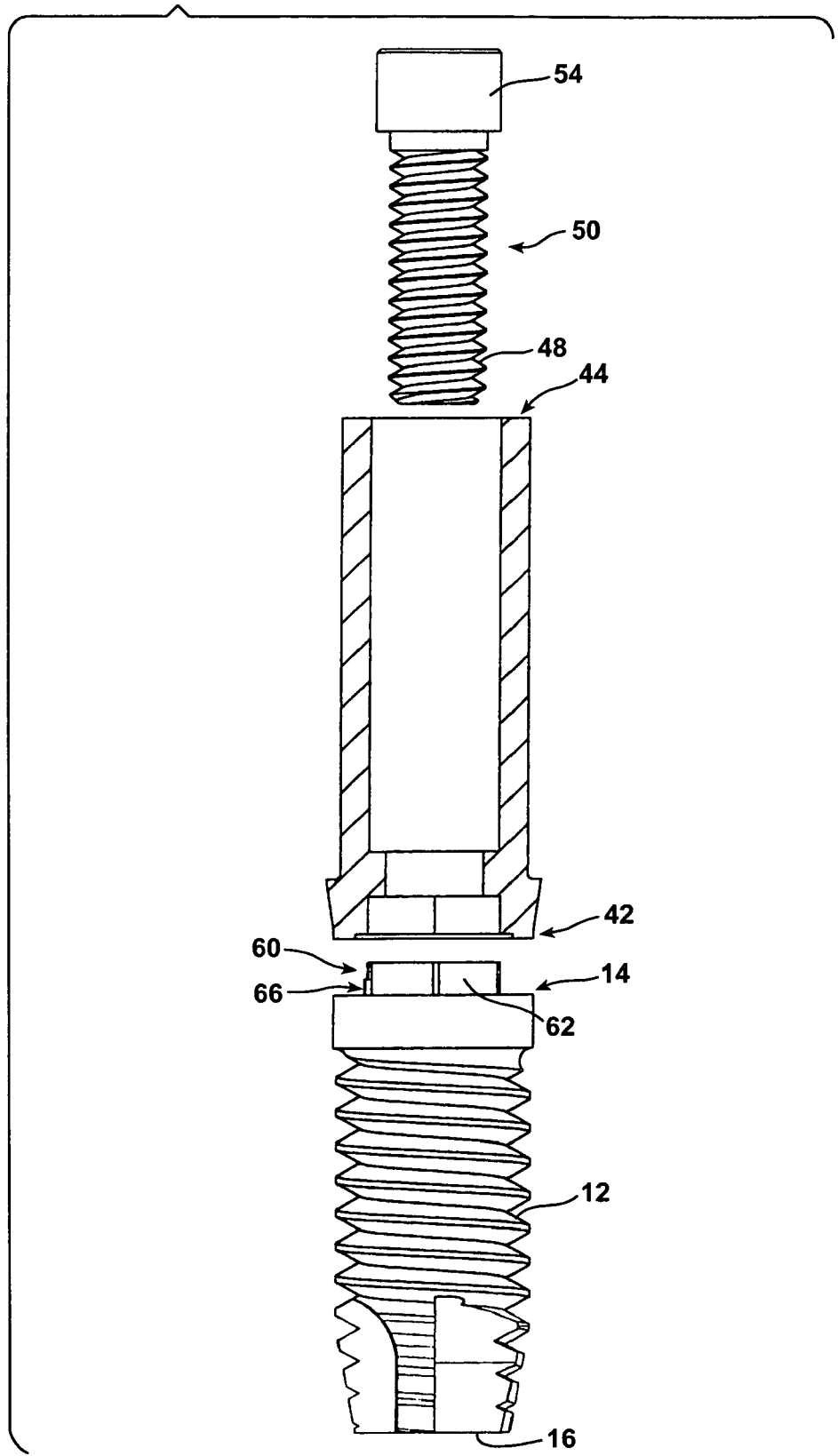
Figure 40:
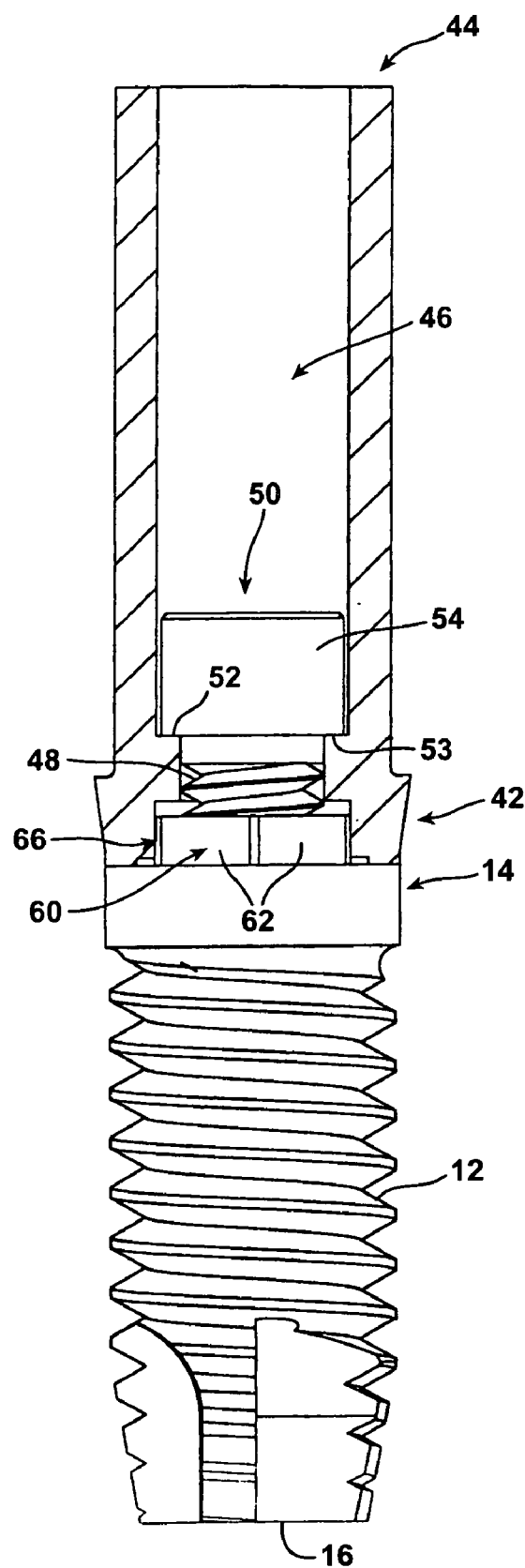

The demarcation between the upper portion 45 of the bore 46 and the internally tapped lower portion 47 of the bore 46 forms an annular bearing ledge or shoulder 52. The annular underside 53 of the head 54 of the clamping screw 50 presses against the bearing surface 52 once the screw 50 is fully advanced longitudinally through the lower, reduced diameter section 47 of the bore 46 and into tight threaded engagement with the internally tapped bore 26 in the implant member 10 when the abutment member 40 and the implant member 10 are joined together, as illustrated in FIG. 20.

At its gingival end 42 the abutment member 40 is provided with a longitudinally extending post 60 of corresponding, mating, noncylindrical shape as the socket 18. The post 60 has a proximal or base end 61 where it meets the main structure of the abutment member 40 and a longitudinally remote distal end 63 that projects down into the depth of the socket 18 when the abutment member 40 is installed on the implant member 10. In all of the embodiments of the invention illustrated in the drawing figures the post 60 has a polygonal shape with a hexagonal cross section with flat, planar walls 62 that are parallel to the axis of alignment 24. For consistency of machining, the corners of the post 60 are flattened by machining slightly so as to create a pair of closely spaced, straight, linear edges 64 between each of the six sides 62 of the post 60. Pairs of closely spaced, mutually parallel, straight, linear post edges 64 delineate the flat, planar post faces or post walls 62 from each other between each of the adjacent planar wall surfaces 62, as illustrated in FIGS. 2 and 2A. The post edges 64 are all parallel to the axis of alignment 24.

In all of the different embodiments of the invention the post 60 is equipped with at least one transversely directed projection protruding therefrom and is otherwise of uniform cross section throughout its length so that the post 60 fits snugly into the socket 18. In the preferred embodiment illustrated in FIGS. 2 and 2A a single projection 66 is defined on a single one of the sides 62 of the post 60. In all of the other embodiments illustrated, the number of transversely directed projections is less, equal to, or more than the number of wall surfaces 62 on the post 60.

In the preferred embodiment of FIGS. 2 and 2A there is a single distinct projection 66 extending perpendicularly out from a single one of the planar wall surfaces 62 and extending longitudinally halfway down the length of the post 60 commencing at the proximal end 61 thereof, remote from the floor 22 of the socket 18. It is to be understood that there can be more than one projection 66. The projection 66 extends laterally across a single one of the post wall surfaces 62 and is shaped as a vertically oriented slab of low, elongated, cross section throughout. This cross section is rectangular considered in the longitudinal, vertical plane passing through the axis of alignment 24, and trapezoidal in all transverse, horizontal planes passing through it and oriented normal to the longitudinal axis of alignment 24.

The slab projection 66 extends outwardly from the planar wall surface 62 only a very extremely short distance, preferably about 0.05 mm. The center, outer face 69 of the slab projection 66 therefore is parallel to and resides at a short distance of about 0.05 mm from the face 62 of the post 60 from which the slab projection transversely projects. The extent of transverse protrusion is small enough so that, as the post 60 is inserted into the socket 18 and the clamping screw 50 advanced to engage the tapped bore 26, the projection 66 can be forced into the socket 18 to create an interference fit between the socket 18 and the post 60. As a consequence, when the clamping screw 50 is fully advanced as far as it will screw into the tapped bore 26 of the implant member 10, the transversely directed projection 66 is force fitted into the cavity of the socket 18 and pressed tightly against the internal cavity wall 28 of the socket 18. The abutment member 40 is thereby firmly immobilized from rotation relative to the implant member 10.

The transversely directed projection or projections on the post 60 may take a variety of different forms. For example, as illustrated in FIGS. 3 and 3A, the transversely directed projections 70 on the post 60 of the abutment member 71 are formed at one or all corner edges of the post 60 and are each shaped as a short, narrow, laterally extending rib or ridge of low, trapezoidal cross section considered in a plane passing through them and perpendicular to the longitudinal axis of alignment 24. This trapezoidal shape is more clearly evident in the perspective view of FIG. 3A. The projections 70 each have a low, short rectangular cross section considered in planes passing through them and containing the longitudinal axis of alignment 24. A separate, narrow, transverse rib 70 is formed between each of the flat, planar faces 62 of the post 60. The ribs 70 are located between the longitudinal, delineating edges 64 which are between the flat wall surfaces 62 of the post 60.

Although of a different configuration than the projection 66 of the embodiment illustrated in FIGS. 2 and 2A, the projections 70 in the embodiment of FIGS. 3 and 3A function in the same manner. That is, when the post 60 is force fitted into the socket 18, the transversely extending projections 70 create an interference fit between the socket 18 and the post 60.

FIG. 4 illustrates another alternative embodiment of the invention in which the transversely directed projections 74 on the abutment member 76 extend laterally across the planar wall faces 62 of the post 60, like the projections 70 in the embodiment of FIG. 3. However, each of the transverse projections 74 has a rounded, semicircular cross-sectional configuration considered in a plane perpendicular to the post wall surface 62 upon which it is formed and containing the axis of alignment 24.

Figure 6:
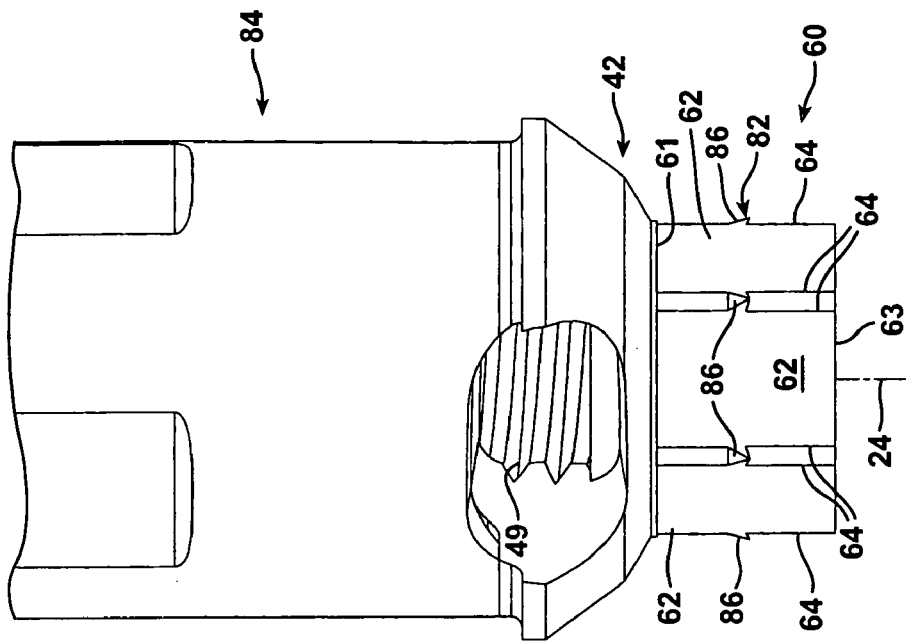
FIG. 6 is an elevational detail, partially broken away, illustrating the gingival end of another alternative embodiment of an abutment member configured to fit into the socket of FIG. 1.
Figure 5:
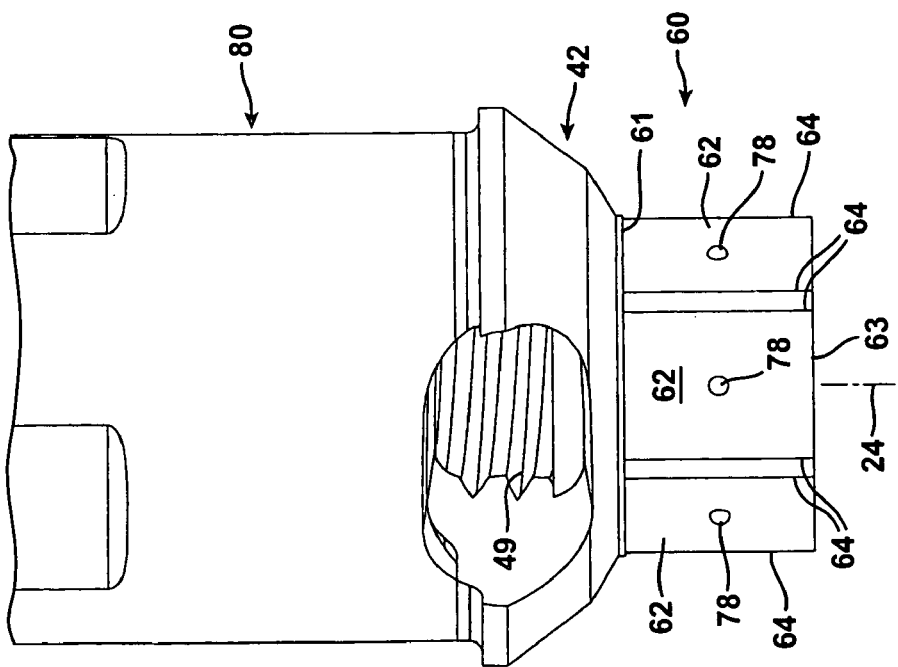
FIG. 5 is an elevational detail, partially broken away, illustrating the gingival end of another alternative embodiment of an abutment member configured to fit into the socket of FIG. 1.

FIG. 5 illustrates another alternative embodiment of the invention in which the transversely projecting protrusions 78 on the abutment member 80 are formed as tiny, hemispherical bubbles located at the centers of each of the post wall surfaces 62. In the embodiment of FIG. 6, the transversely extending projections 82 on the abutment member 84 are formed as barbs at the demarcations between the flat post wall surfaces 62 at each of the corners thereof. The barbs 82 are inclined outwardly away from the post wall surfaces 62 and toward the socket 18 in the implant member 10. The planar, outer faces 86 of the barbs 82 diverge outwardly from the post 60 and are inclined outwardly toward the socket 18.

Figure 7:
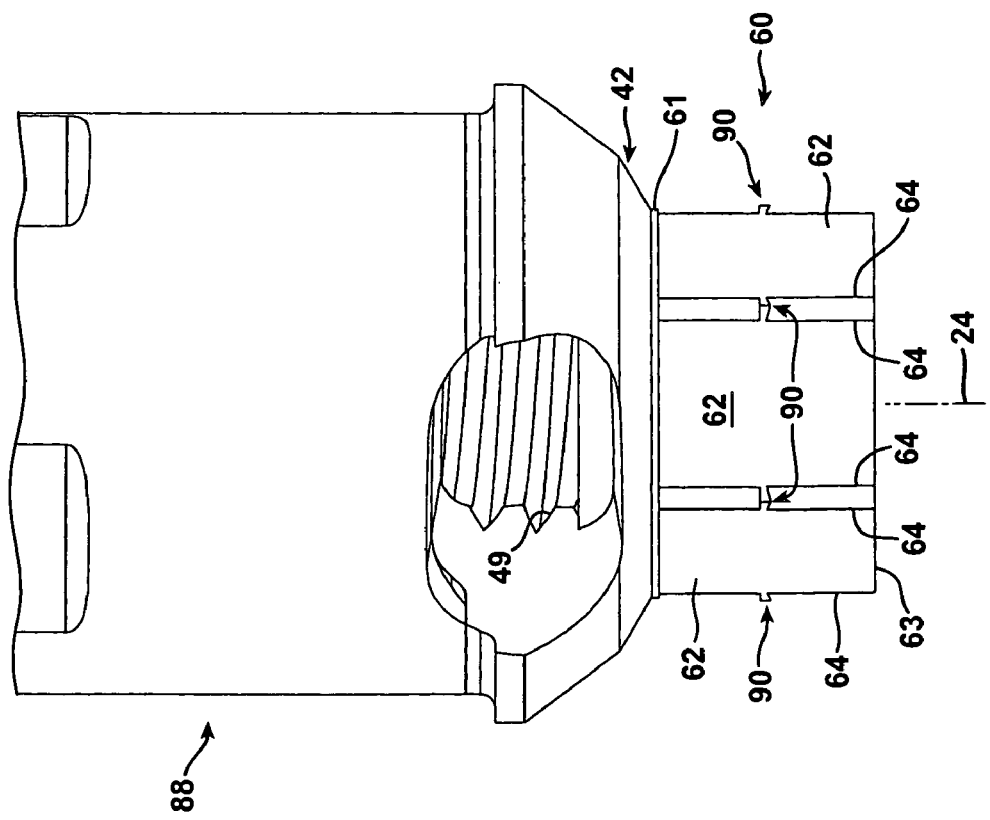
FIG. 7 is an elevational detail, partially broken away, illustrating the gingival end of another alternative embodiment of an abutment member configured to fit into the socket of FIG. 1.

FIG. 7 illustrates another abutment member 88 having six transversely, outwardly directed projections 90 located midway along the length of the post 60 and between the pairs of edges 64 delineating the demarcations between the flat post wall surfaces or sides 62. The projections 90 are shaped as tiny barbs having the cross section of a parallelogram considered in planes passing through them and containing the longitudinal axis of alignment 24 in which the minor bases of the parallelogram structure are located at the surface of the post 60, while the major bases of those structures are located outboard in a transverse direction and parallel to the flat surfaces of the post 60.

Figure 8:
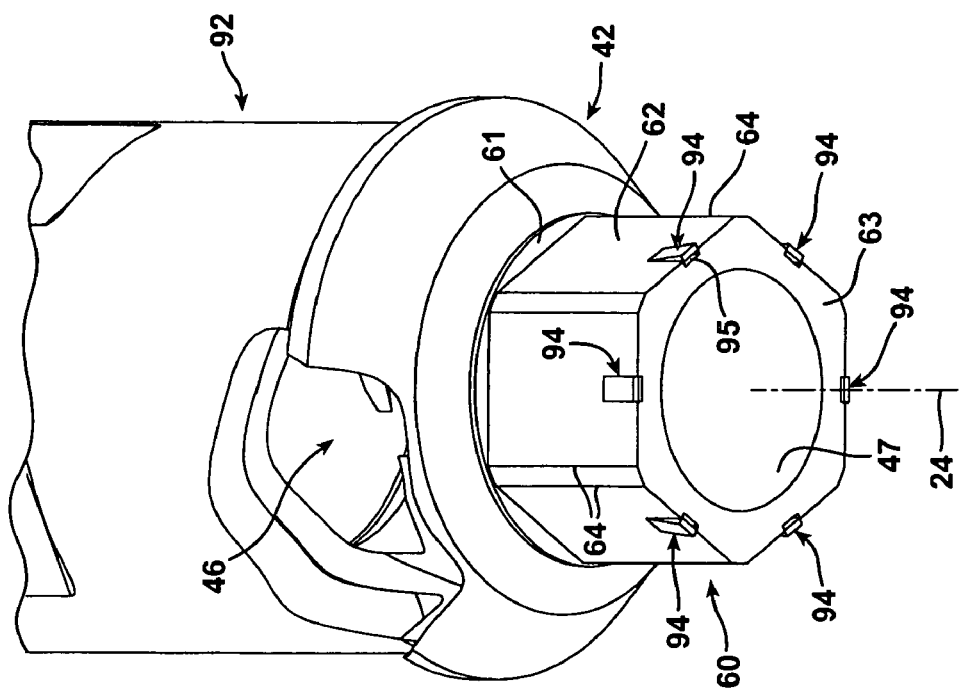
FIG. 8 is a perspective detail, partially broken away, illustrating the gingival end of another alternative embodiment of an abutment member configured to fit into the socket of FIG. 1.

In the abutment 92 shown in FIG. 8 the post 60 is equipped with transversely outwardly directed barbs 94 that are inclined outwardly and away from the flat wall surfaces 62 of the post 60 and which are formed as tangs at the distal end 63 of the post 60 from short, longitudinally extending channels 95 of rectangular cross section in planes normal to the longitudinal axis of alignment 24. The tangs or barbs 94 are inclined outwardly from the flat wall surfaces 62 at the distal end 63 of the post 60 proceeding toward the socket 18.

Figure 9:
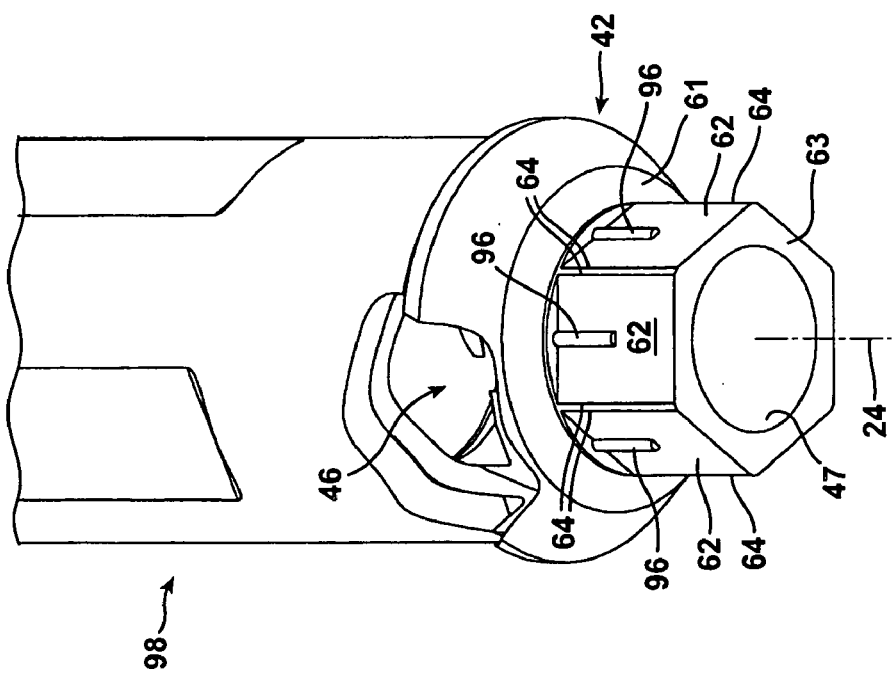
FIG. 9 is a perspective detail, partially broken away, illustrating the gingival end of another alternative embodiment of an abutment member configured to fit into the socket of FIG. 1.

In the embodiment of the invention illustrated in FIG. 9 the transversely extending projections 96 of the abutment member 98 are formed as longitudinally extending ribs at the centers of each of the flat post wall surfaces or sides 62. Each of the projections 96 has a rectangular cross section considered in a plane bisecting and perpendicular to the wall surface upon which it is formed and containing the longitudinal axis of alignment 24. Each of the transversely extending projections 96 has a uniform, semicircular cross section considered in a plane passing through it and perpendicular to the longitudinal axis of alignment 24. The transversely extending projections 96 are located at the proximal end 61 of the post 60 and extend only halfway down the length of the post 60 toward the distal end 63 thereof.

Figure 10:
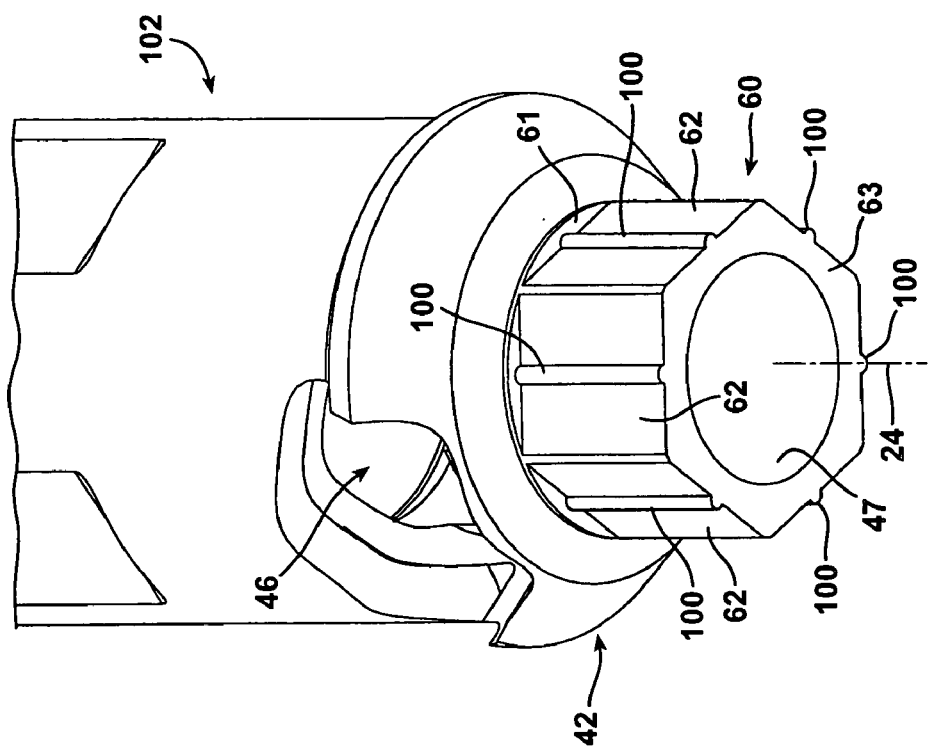
FIG. 10 is a perspective detail, partially broken away, illustrating the gingival end of another alternative embodiment of an abutment member configured to fit into the socket of FIG. 1.

In the embodiment of FIG. 10 the transversely extending projections 100 on the abutment member 102 have the same shape and location as the projections 96 in the embodiment of FIG. 9. However, they extend the entire length of the post 60 from the proximal end 61 to the distal end 63 thereof.

Figure 11:
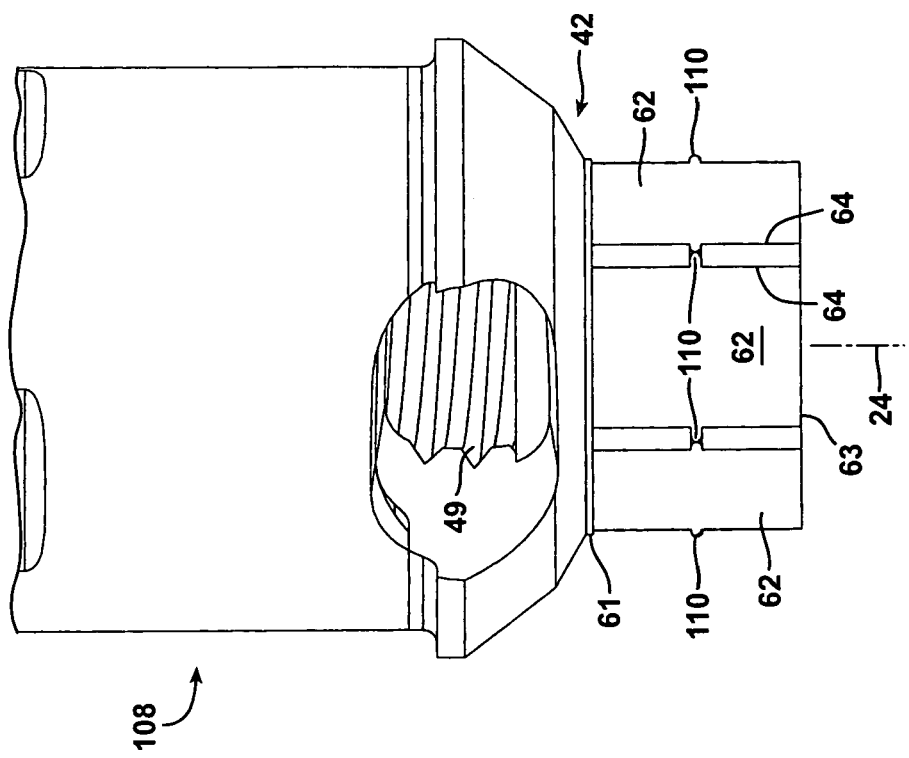
FIG. 11 is a perspective detail, partially broken away, illustrating the gingival end of another alternative embodiment of an abutment member configured to fit into the socket of FIG. 1.

In the abutment member 104 shown in FIG. 11 the transversely extending projections 106 extend longitudinally down the centers of the faces 62 of the post 60, but have a narrow, rectangular cross section when considered in a plane passing through them and perpendicular to the axis of alignment 24. This is in contrast to the rounded, semicircular cross section of the projections 100 in the embodiment of FIG. 10.

Figure 12:
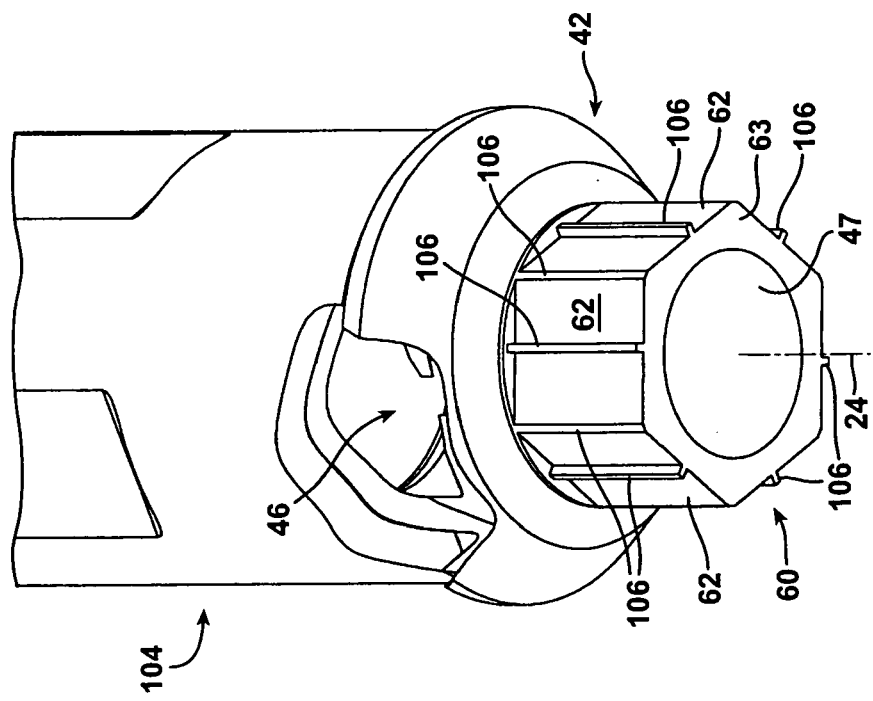
FIG. 12 is an elevational detail, partially broken away, illustrating the gingival end of another alternative embodiment of an abutment member configured to fit into the socket of FIG. 1.

In the embodiment of the invention illustrated in FIG. 12 the abutment member 108 is provided with transversely extending tangs 110 which are located at the corners of the post 60 between the sets of edges 64 thereof and between the flat wall surfaces 62. The projections 110 have a rounded, semicircular cross section when viewed in planes passing through them and containing the axis of alignment 24. The projections 110 have a triangular cross-sectional configuration when considered in planes passing through them and oriented perpendicular to the axis of alignment 24.

Figure 13:
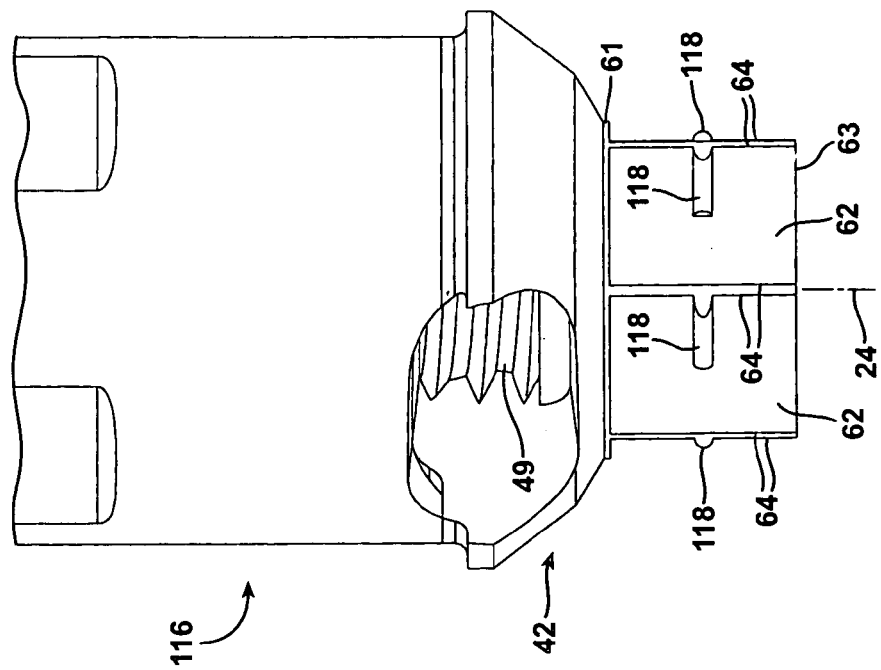
FIG. 13 is an elevational detail, partially broken away, illustrating the gingival end of another alternative embodiment of an abutment member configured to fit into the socket of FIG. 1.

In the abutment member 112 illustrated in FIG. 13 the transversely extending projections 114 are configured as ribs extending partway across each of the flat post wall surfaces 62. Each of the projections 114 has a somewhat elongated rectangular cross section when considered in a plane passing through it and perpendicular to the longitudinal axis of alignment 24 and a short, narrow rectangular cross section considered in a plane bisecting it and containing the longitudinal axis of alignment 24.

Figure 14:
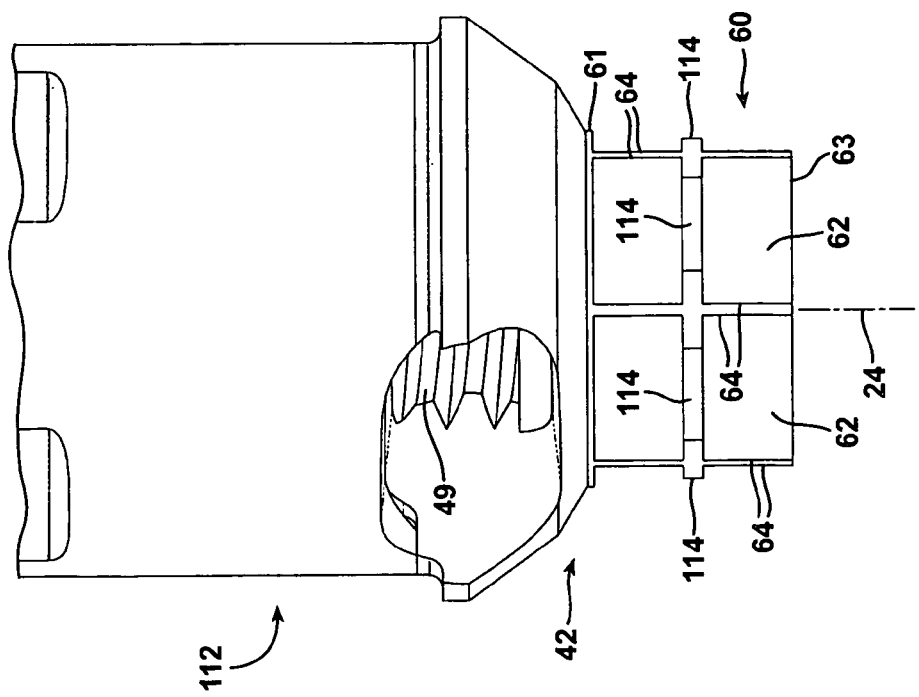
FIG. 14 is an elevational detail, partially broken away, illustrating the gingival end of another alternative embodiment of an abutment member configured to fit into the socket of FIG. 1.
Figure 17:
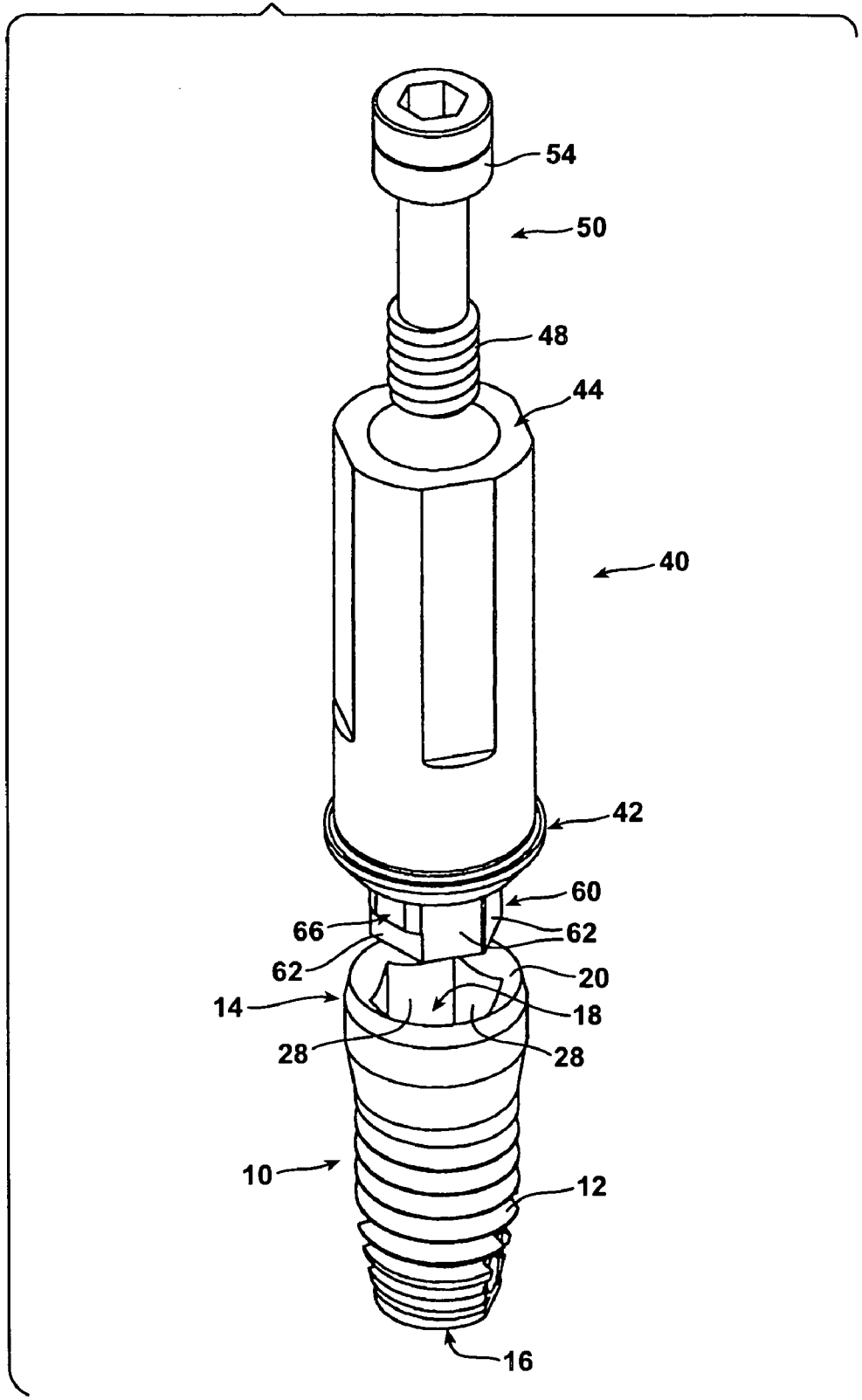
FIG. 17 is an exploded perspective view illustrating the implant member of FIG. 1 and the abutment member of FIG. 2 prior to attachment to each other.
Figure 18:
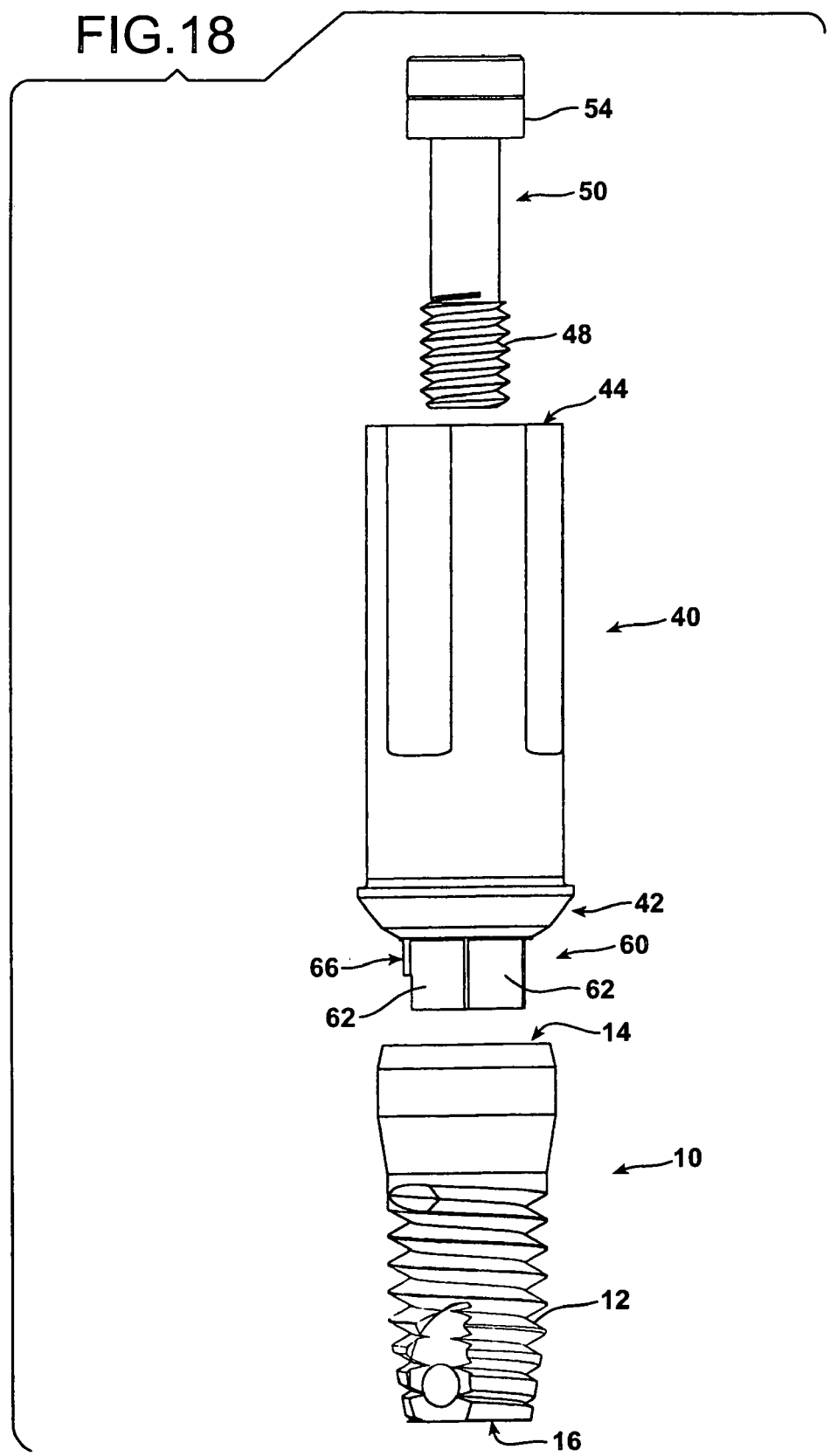
FIG. 18 is an exploded side elevational view of FIG. 16.
Figure 19:
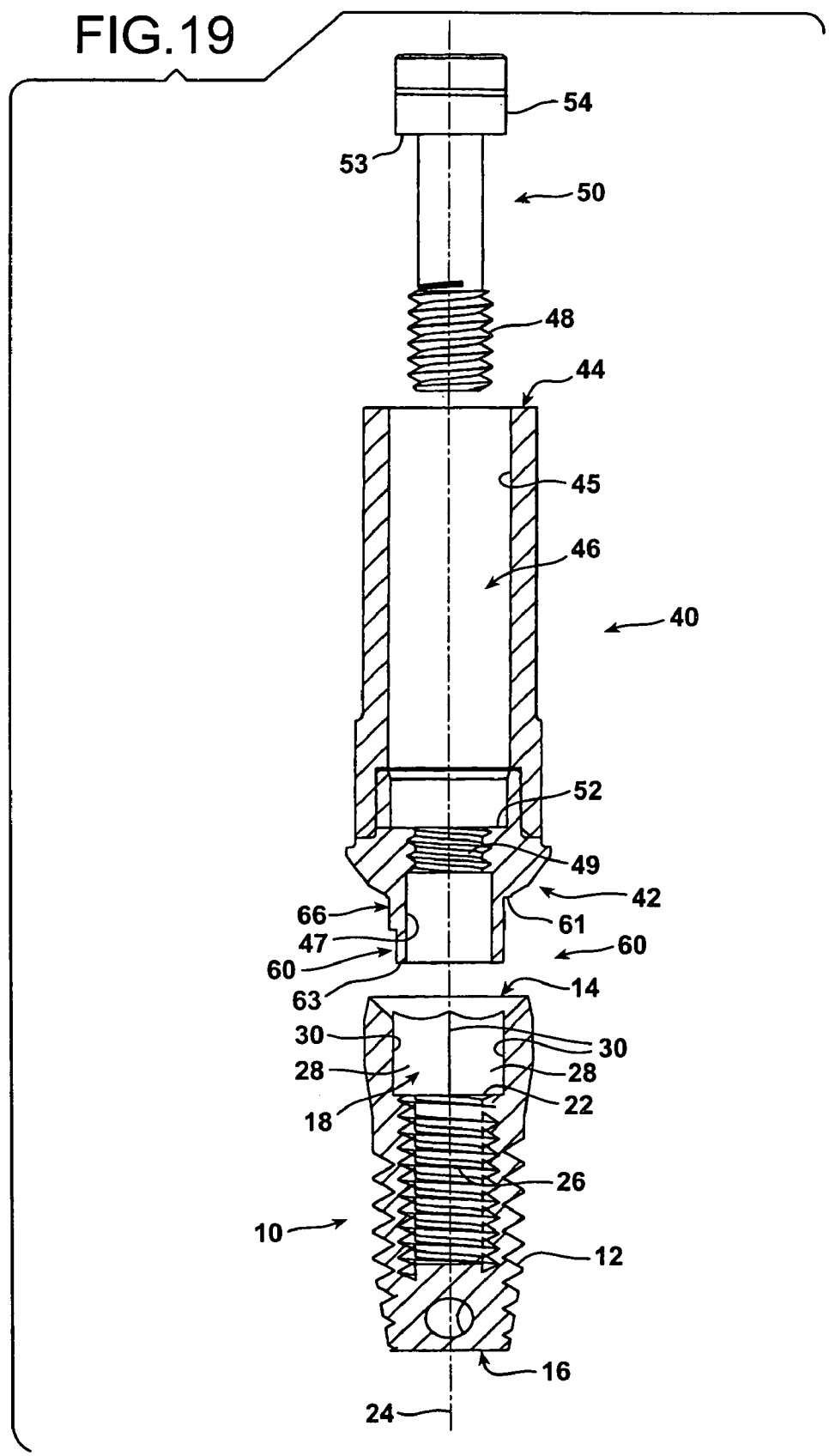
FIG. 19 is an exploded side sectional view of FIG. 17.

In the abutment members 116 illustrated in FIG. 14, the transversely extending projections 118 extend from one of the edges 64 of the pairs of edges forming the demarcation between the post wall faces 62 laterally halfway across the width of the post wall face 62 upon which it is formed. The transverse projections 118 have a trapezoidal cross-sectional configuration considered in a plane bisecting them and oriented perpendicular to the longitudinal axis of alignment 24. Each of the transverse projections 118 has a rounded, semicircular cross-sectional configuration considered in a plane passing through it and containing the axis of alignment 24.

In the abutment member 120 shown in FIG. 15 each of the transverse projections 122 extends only halfway across the post wall 62 upon which it is formed and has a narrow, rectangular configuration considered in a plane passing through it and containing the axis of alignment 24. In a plane perpendicular thereto normal to the axis of alignment 24 and passing through the transverse projections 122, each projection 122 has an elongated trapezoidal cross-sectional configuration. The transverse projections 126 on the post 60 of the abutment 128 shown in FIG. 16 are configured and located the same as the projections 106 on the abutment 104 shown in FIG. 11. However, the projections 126 extend only half way down the length of the post 60 from the proximal end 61 thereof.

In all of the embodiments illustrated in FIGS. 1 through 20 the post 60 is formed upon the gingival end 42 of the abutment member while the socket 18 is defined in the gingival end 14 of the implant member 10. However, the implant system of the invention can be constructed in a manner such that the locations of the post 60 and socket 18 are reversed. That is, the socket 18 can be defined in the gingival end 42 of the abutment member while the post 60 may be formed on the gingival end 14 of the implant member 10. Drawing FIGS. 21 through 40 illustrate this reverse construction and correspond, respectively, to drawing FIGS. 1 through 20, respectively.

Undoubtedly, numerous variations and modifications of the invention will become readily apparent to those familiar with dental implant systems employing mating implant and abutment members. For example, there are numerous other different shapes in which the transversely extending projections from the post at the gingival end of one of the abutment and implant members can be formed, in addition to those illustrated in the drawing figures. The critical feature of the invention is that the post at the gingival end of the implant or abutment member upon which it is formed must have at least one transversely directed projection protruding therefrom and is otherwise of uniform cross section throughout. In this way the post fits snugly into the socket with the transverse projection or projections therefrom pressing against the interior walls of the socket to create an interference fit between the socket and the post. Accordingly, the scope of the invention should not be construed as limited to the specific embodiments depicted and described, but rather is defined in the claims appended hereto.

I claim:

1. In combination, an endosseous dental implant member and a mating abutment member both having mutually facing gingival ends, and said gingival end of one of said members has a socket of noncylindrical shape and uniform cross section throughout defined therein and facing the gingival end of the other of said members, and the other of said members has at its gingival end a post of corresponding, mating, noncylindrical shape wherein said socket and said post both have mating polygonal shapes forming planar post wall surfaces with straight, longitudinally extending edges therebetween and planar socket wall surfaces with straight, longitudinal edges therebetween, and said post has a longitudinal axis of alignment and is equipped with at least one transversely directed projection protruding from at least one of said post wall surfaces and is otherwise of uniform cross section throughout and said transversely directed projection extends longitudinally along only a portion of said post and laterally across the entire post wall surface from which it protrudes and has a rectangular cross section considered in a plane containing said longitudinal axis of alignment and perpendicular to the planar post wall surface upon which it is formed and a trapezoidal cross section considered in a plane passing through it and oriented normal to said longitudinal axis of alignment, and wherein said post fits snugly into said socket with an interference fit between said post and said socket so that said at least one transversely directed projection is force fitted into said socket pressed tightly against a facing socket wall surface of said socket.

2. A combination according to claim 1 wherein said post is formed on said gingival end of said abutment member and said socket is formed in said gingival end of said implant member.

3. A combination according to claim 1 wherein said post is formed on said gingival end of said implant member and said socket is formed in said gingival end of said abutment member.

4. A combination according to claim 1 further comprising a plurality of said projections on said post.

5. A combination according to claim 4 wherein said projections are directed perpendicularly out from said post.

6. A combination according to claim 1 further comprising a plurality of projections as aforesaid wherein said projections are formed on said planar faces of said post as laterally extending ribs.

7. In combination, an endosseous dental implant member and a mating abutment member both having mutually facing gingival ends, and said gingival end of one of said members has a polygonal socket shape and uniform cross section throughout defined therein with planar socket walls and facing said gingival end of said other of said members, and said other of said members has at its gingival end a post with a longitudinal axis of alignment and of corresponding size and polygonal shape as said socket and with planar post walls so as to seat snugly into said socket and said post has at least one transversely projecting protrusion and said transversely directed protrusion extends longitudinally along only a portion of said post and laterally entirely across the post wall surface from which it protrudes and has a rectangular cross section considered in a plane containing said longitudinal axis of alignment and perpendicular to the planar post wall surface upon which it is formed and a trapezoidal cross section considered in a plane passing through it and oriented normal to said longitudinal axis of alignment, and said post fits into said socket with an interference fit that obstructs twisting of said post within said socket and said post is otherwise of uniform cross section throughout.

8. In a dental implant system employing an endosseous dental implant member having a gingival end and a mating abutment member having a gingival end facing said gingival end of said dental implant member and a socket of uniform, polygonal cross section throughout having planar socket wall surfaces is defined into one of said members in said gingival end thereof and a post extends from said gingival end of said other member, and said post has a polygonal cross section matching that of said socket and corresponding planar post wall surfaces so as to allow said post to fit snugly into said socket along a common axis of alignment, the improvement comprising at least one transversely directed projection formed on one of said post wall surfaces of said post that is short enough to allow said post to be completely seated in said socket and said transversely directed projection extends longitudinally along only a portion of said post and laterally entirely across said post wall surface from which it protrudes and has a rectangular cross section considered in a plane containing said longitudinal axis of alignment and perpendicular to said planar post wall surface upon which it is formed and a trapezoidal cross section considered in a plane passing through it and oriented normal to said longitudinal axis of alignment and said transversely directed projection extends radially relative to said common axis of alignment a sufficient distance to create an interference fit between said post and said socket.

\* \* \* \* \*